United States Patent
Sharma et al.

(10) Patent No.: US 8,022,249 B2
(45) Date of Patent: Sep. 20, 2011

(54) COMPOUNDS FOR THE TREATMENT OF METABOLIC DISORDERS

(75) Inventors: Shalini Sharma, Gaithersburg, MD (US); Reid W. von Borstel, Potomac, MD (US)

(73) Assignee: Wellstat Therapeutics Corporation, Gaithersburg, MD (US)

( * ) Notice: Subject to any disclaimer, the term of this patent is extended or adjusted under 35 U.S.C. 154(b) by 548 days.

(21) Appl. No.: 11/909,120

(22) PCT Filed: Mar. 31, 2006

(86) PCT No.: PCT/US2006/012050
§ 371 (c)(1),
(2), (4) Date: Sep. 19, 2007

(87) PCT Pub. No.: WO2006/127133
PCT Pub. Date: Nov. 30, 2006

(65) Prior Publication Data
US 2009/0234016 A1   Sep. 17, 2009

Related U.S. Application Data

(60) Provisional application No. 60/667,457, filed on Apr. 1, 2005.

(51) Int. Cl.
C07C 259/04 (2006.01)
A61K 31/19 (2006.01)

(52) U.S. Cl. ......... 562/621; 564/182; 514/575; 514/617

(58) Field of Classification Search ........... 564/182; 560/621; 514/575, 617; 562/621
See application file for complete search history.

(56) References Cited

U.S. PATENT DOCUMENTS

| | | | |
|---|---|---|---|
| 4,053,607 A * | 10/1977 | Thorne et al. | 514/345 |
| 4,067,892 A | 1/1978 | Thorne et al. | |
| 4,188,338 A | 2/1980 | Bruins et al. | |
| 6,858,602 B2 | 2/2005 | Sharma et al. | |
| 6,916,848 B2 | 7/2005 | Sharma | |
| 6,924,314 B2 | 8/2005 | Sharma et al. | |
| 6,946,491 B2 | 9/2005 | Sharma et al. | |
| 7,012,071 B2 | 3/2006 | Sharma et al. | |
| 7,041,659 B2 | 5/2006 | Sharma | |
| 7,045,541 B2 | 5/2006 | Sharma | |
| 7,101,910 B2 | 9/2006 | Sharma et al. | |
| 2005/0090555 A1 | 4/2005 | Sharma et al. | |
| 2005/0256333 A1 | 11/2005 | Sharma et al. | |
| 2006/0014784 A1 | 1/2006 | Hodge et al. | |
| 2006/0035970 A1 | 2/2006 | Hodge et al. | |
| 2006/0247309 A1 | 11/2006 | Hodge et al. | |
| 2007/0105955 A1 | 5/2007 | Hodge et al. | |
| 2007/0105958 A1 | 5/2007 | Sharma et al. | |
| 2007/0173544 A1 | 7/2007 | Hodge et al. | |
| 2007/0249696 A1 | 10/2007 | Sharma et al. | |
| 2007/0249719 A1 | 10/2007 | Sharma et al. | |
| 2007/0265322 A1 | 11/2007 | Sharma et al. | |
| 2007/0282003 A1 | 12/2007 | Sharma et al. | |
| 2008/0015209 A1 | 1/2008 | Sharma et al. | |
| 2008/0015254 A1 | 1/2008 | Sharma et al. | |
| 2008/0021109 A1 | 1/2008 | Sharma et al. | |
| 2008/0027229 A1 | 1/2008 | Sharma et al. | |

FOREIGN PATENT DOCUMENTS

| | | |
|---|---|---|
| DE | 2459468 | 7/1975 |
| FR | 5.035 M | 5/1967 |
| GB | 1488330 | 10/1977 |
| JP | 52025734 | 2/1977 |
| JP | 56115747 | 9/1981 |
| JP | 57-149254 * | 9/1982 |

(Continued)

OTHER PUBLICATIONS

Goff et al. Prevention of cardiovascular disease in persons with type 2 diabetes mellitus: current knowledge and rationale for the action to control cardiovascular risk in diabetes (ACCORD) Trial. Am J Cardiol. 2007;99(12A):$4-$20, abstract only.*
Younis et al. The prevention of type 2 diabetes mellitus: recent advances. Q J Med 2004; 97:451-455.*
Knowler et al. Persepectives in diabetes: Preventing non-insulin dependent diabetes. Diabetes. 1995;44:483-488.*
Calza et al. Insulin resistance and diabetes mellitus in HIV-infected patients receiving antiretroviral therapy. Metabolic Syndrome and Related Disorders. 2004;2(4):241-250; abstract only.*
Chen et al. Lipodystrophy in human immunodeficiency virus-infected patients. J Clin Endocrinol Metab 2002;87:4845-4856.*

(Continued)

*Primary Examiner* — Shailendra Kumar
(74) *Attorney, Agent, or Firm* — Lewis J. Kreisler

(57) ABSTRACT

Compounds useful for the treatment of various metabolic disorders, such as insulin resistance syndrome, diabetes, hyperlipidemia, fatty liver disease, cachexia, obesity, atherosclerosis and arteriosclerosis are disclosed. wherein n is 1 or 2; m is 0, 1, 2, 3, 4 or 5; q is 0 or 1; t is 0 or 1; $R^1$ is alkyl having from 1 to 3 carbon atoms; $R^2$ is hydrogen, halo, alkyl having from 1 to 3 carbon atoms, or alkoxy having from 1 to 3 carbon atoms; $R^3$ is hydrogen or —$(CH_2)_g$OH wherein g is 0, 1 or 2; $R^4$ is hydrogen, methyl or ethyl; A is phenyl, unsubstituted or substituted by 1 or 2 groups selected from: halo, alkyl having 1 or 2 carbon atoms, perfluoromethyl, alkoxy having 1 or 2 carbon atoms, and perfluoromethoxy; or cycloalkyl having from 3 to 6 ring carbon atoms wherein the cycloalkyl is unsubstituted or one or two ring carbons are independently mono-substituted by methyl or ethyl; or a 5 or 6 membered heteroaromatic ring having 1 or 2 ring heteroatoms selected from N, S and O and the heteroaromatic ring is covalently bound to the remainder of the compound of formula I by a ring carbon; or a pharmaceutically acceptable salt of the compound.

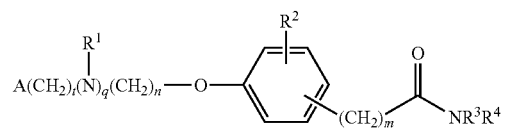

(I)

23 Claims, No Drawings

FOREIGN PATENT DOCUMENTS

| | | |
|---|---|---|
| JP | 01216961 | 8/1989 |
| WO | 95/24379 A1 | 9/1995 |
| WO | 02/100341 A2 | 12/2002 |
| WO | 03/106380 A2 | 12/2003 |
| WO | 2004/007429 A1 | 1/2004 |
| WO | 2004/073611 A2 | 9/2004 |
| WO | 2004/091486 A2 | 10/2004 |
| WO | 2007/117791 A2 | 10/2007 |
| WO | 2008/022267 A2 | 2/2008 |

OTHER PUBLICATIONS

Adams et al. Treatment of hyperlipidemia in nonalcoholic fatty liver disease: fat for thought. Indian Society of Gastroenterology. .2004. 23:127-128.*

Worman HJ. Alcoholic liver disease, http:llcpmcnet.columbia. eduldeptlgilalcohol.html. Electronic copy, 1998, pp. 1-3.*

Barrett, et al., "Phenol Oxidation and Biosynthesis. Part 27. Reactions of Relevance to the Formation of Erysodienone in vitro", J.C.S. Perkin I, 1979, pp. 662-668.

Veronese, et al., "Ozonolysis of derivatives of 7-hydroxytryptophan", Gazz. Chim. Ital., vol. 97, No. 1, pp. 18-24, 1967. (Abstract).

Chemical Abstract DN 117:251790, also cited as WO92/12123.

Chemical Abstract DN 113:115839, also cited as Synthetic Communications, 20/5, 773-81, 1990.

Younis, et al., "The prevention of type 2 diabetes mellitus: recent advances", QJ Med., vol. 97, pp. 451-455, 2004.

Goff, et al., "Prevention of Cardiovascular Disease in Persons with type 2 diabetes Mellitus: Current Knowledge and Rational for the Action to Control Cardiovascular Risk in Diabetes (ACCORD) Trial", AM J Cardiol., 99(12A): S4-S20, 2007. (Abstract).

Knowler, et al., "Perspectives in Diabetes: Preventing Non-Insulin-Dependent Diabetes", Diabetes, vol. 44, pp. 483-488, 1995.

Pending (as of Mar. 24, 2008) claims from U.S. Appl. No. 11/772,515.

Pending (as of Mar. 24, 2008) claims from U.S. Appl. No. 11/772,520.

Pending (as of Mar. 24, 2008) claims from U.S. Appl. No. 11/772,560.

Coburn, et al., "Potential Salicylamide Antiplague Agents: In Vitro Antibacterial Activity against *Actinomyces viscosus*", J. Med. Chem, vol. 24, pp. 1245-1249, 1981.

\* cited by examiner

COMPOUNDS FOR THE TREATMENT OF METABOLIC DISORDERS

BACKGROUND OF THE INVENTION

Diabetes mellitus is a major cause of morbidity and mortality. Chronically elevated blood glucose leads to debilitating complications: nephropathy, often necessitating dialysis or renal transplant; peripheral neuropathy; retinopathy leading to blindness; ulceration of the legs and feet, leading to amputation; fatty liver disease, sometimes progressing to cirrhosis; and vulnerability to coronary artery disease and myocardial infarction.

There are two primary types of diabetes. Type I, or insulin-dependent diabetes mellitus (IDDM) is due to autoimmune destruction of insulin-producing beta cells in the pancreatic islets. The onset of this disease is usually in childhood or adolescence. Treatment consists primarily of multiple daily injections of insulin, combined with frequent testing of blood glucose levels to guide adjustment of insulin doses, because excess insulin can cause hypoglycemia and consequent impairment of brain and other functions.

Type II, or noninsulin-dependent diabetes mellitus (NIDDM) typically develops in adulthood. NIDDM is associated with resistance of glucose-utilizing tissues like adipose tissue, muscle, and liver, to the actions of insulin. Initially, the pancreatic islet beta cells compensate by secreting excess insulin. Eventual islet failure results in decompensation and chronic hyperglycemia. Conversely, moderate islet insufficiency can precede or coincide with peripheral insulin resistance. There are several classes of drugs that are useful for treatment of NIDDM: 1) insulin releasers, which directly stimulate insulin release, carrying the risk of hypoglycemia; 2) prandial insulin releasers, which potentiate glucose-induced insulin secretion, and must be taken before each meal; 3) biguanides, including metformin, which attenuate hepatic gluconeogenesis (which is paradoxically elevated in diabetes); 4) insulin sensitizers, for example the thiazolidinedione derivatives rosiglitazone and pioglitazone, which improve peripheral responsiveness to insulin, but which have side effects like weight gain, edema, and occasional liver toxicity; 5) insulin injections, which are often necessary in the later stages of NIDDM when the islets have failed under chronic hyperstimulation.

Insulin resistance can also occur without marked hyperglycemia, and is generally associated with atherosclerosis, obesity, hyperlipidemia, and essential hypertension. This cluster of abnormalities constitutes the "metabolic syndrome" or "insulin resistance syndrome". Insulin resistance is also associated with fatty liver, which can progress to chronic inflammation (NASH; "nonalcoholic steatohepatitis"), fibrosis, and cirrhosis. Cumulatively, insulin resistance syndromes, including but not limited to diabetes, underlie many of the major causes of morbidity and death of people over age 40.

Despite the existence of such drugs, diabetes remains a major and growing public health problem. Late stage complications of diabetes consume a large proportion of national health care resources. There is a need for new orally active therapeutic agents which effectively address the primary defects of insulin resistance and islet failure with fewer or milder side effects than existing drugs.

Currently there are no safe and effective treatments for fatty liver disease. Therefore such a treatment would be of value in treating this condition.

WO 02/100341 (Wellstat Therapeutics Corp.) discloses certain hydroxyamide-substituted compounds and amide-substituted compounds, for example 4-(3-(2,6-Dimethylbenzyloxy)phenyl)-4-oxobutyramide.

SUMMARY OF THE INVENTION

This invention provides a compound or pharmaceutically acceptable salt thereof as described below. This invention provides the use of the compound or pharmaceutically acceptable salt thereof described below in the manufacture of a medicament for the treatment of insulin resistance syndrome, diabetes, cachexia, hyperlipidemia, fatty liver disease, obesity, atherosclerosis or arteriosclerosis. This invention provides methods of treating a mammalian subject with insulin resistance syndrome, diabetes, cachexia, hyperlipidemia, fatty liver disease, obesity, atherosclerosis or arteriosclerosis comprising administering to the subject an effective amount of the compound or pharmaceutically acceptable salt described below. This invention provides a pharmaceutical composition comprising the compound or pharmaceutically acceptable salt described below and a pharmaceutically acceptable carrier.

The compound or salt in accordance with this invention is a compound of Formula I:

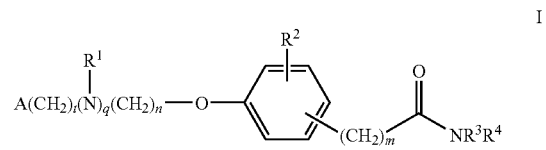

wherein n is 1 or 2; m is 0, 1, 2, 3, 4 or 5; q is 0 or 1; t is 0 or 1; $R^1$ is alkyl having from 1 to 3 carbon atoms; $R^2$ is hydrogen, halo, alkyl having from 1 to 3 carbon atoms, or alkoxy having from 1 to 3 carbon atoms; $R^3$ is hydrogen or —$(CH_2)_g$OH wherein g is 0, 1 or 2; $R^4$ is hydrogen, methyl or ethyl; A is phenyl, unsubstituted or substituted by 1 or 2 groups selected from: halo, alkyl having 1 or 2 carbon atoms, perfluoromethyl, alkoxy having 1 or 2 carbon atoms, and perfluoromethoxy; or cycloalkyl having from 3 to 6 ring carbon atoms wherein the cycloalkyl is unsubstituted or one or two ring carbons are independently mono-substituted by methyl or ethyl; or a 5 or 6 membered heteroaromatic ring having 1 or 2 ring heteroatoms selected from N, S and O and the heteroaromatic ring is covalently bound to the remainder of the compound of formula I by a ring carbon; or a pharmaceutically acceptable salt of the compound.

The compounds and salts of Formula I have activity in the biological activity assay described below, which is an established animal model of human diabetes and insulin resistance syndrome. Therefore such compounds and salts would be useful in the treatment of diabetes and insulin resistance syndrome. The exemplified compounds that were tested demonstrated activity in such assay.

DETAILED DESCRIPTION OF THE INVENTION

Definitions

As used herein the term "alkyl" means a linear or branched-chain alkyl group. An alkyl group identified as having a certain number of carbon atoms means any alkyl group having the specified number of carbons. For example, an alkyl having three carbon atoms can be propyl or isopropyl; and alkyl having four carbon atoms can be n-butyl, 1-methylpropyl, 2-methylpropyl or t-butyl.

As used herein the term "halo" refers to one or more of fluoro, chloro, bromo, and iodo.

As used herein the term "perfluoro" as in perfluoromethyl or perfluoromethoxy, means that the group in question has fluorine atoms in place of all of the hydrogen atoms.

As used herein "Ac" refers to the group $CH_3C(O)$—.

Certain chemical compounds are referred to herein by their chemical name or by the two-letter code shown below. Compounds CT, CU and CV are included within the scope of Formula I shown above.

BI 4-(3-(2,6-Dimethylbenzyloxy)phenyl)-4-oxobutyric acid
CT N-Hydroxy-2-[3-(2,6-dimethylbenzyloxy)phenyl]acetamide
CU 2-[3-(2,6-Dimethylbenzyloxy)phenyl]acetamide
CV N-(2-Hydroxyethyl)-2-[3-(2,6-dimethylbenzyloxy)phenyl]acetamide As used herein the transitional term "comprising" is open-ended. A claim utilizing this term can contain elements in addition to those recited in such claim.

Compounds of the Invention

In an embodiment of the compound, salt, use, method or pharmaceutical composition described above, m is 1; n is 1; q is 0; t is 0; $R^2$ is hydrogen; $R^4$ is hydrogen; and A is phenyl, unsubstituted or substituted by 1 or 2 groups selected from: halo, alkyl having 1 or 2 carbon atoms, perfluoromethyl, alkoxy having 1 or 2 carbon atoms, and perfluoromethoxy. In a more specific embodiment, A is 2,6-dimethylphenyl. Examples of such compounds include Compounds CT, CU, and CV.

In a preferred embodiment of this invention, the compound or salt of Formula I is in substantially (at least 98%) pure form.

Reaction Schemes

The compound of formula I where m is 0 to 5, q is 0 or 1, t is 0 or 1, and n is 1 or 2, $R^1$ is an alkyl having 1 to 3 carbon atoms, $R^2$ is hydrogen, halo, alkoxy having from 1 to 3 carbon atoms or alkyl having from 1 to 3 carbon atoms, $R^3$ is hydrogen or —$(CH_2)_g$OH wherein g is 0 to 2 and $R^4$ is hydrogen, methyl or ethyl, i.e. compounds of formula:

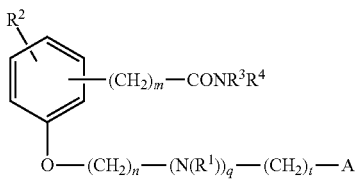

wherein A is described as above, can be prepared from the compound of the formula,

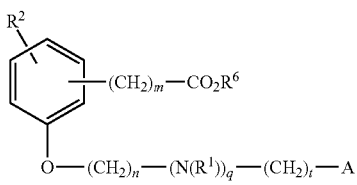

via reaction scheme 1.

In the reaction scheme of Scheme 1, A, t, n, m, q, $R^1$, $R^3$, $R^4$ and $R^2$ are as above. $R^6$ is hydrogen.

The compound of formula I where $R^3$ is hydrogen and $R^4$ is hydrogen, can be prepared via reaction step (a) by first activating the acid by for example, benzotriazole-1-yloxytrispyrrolidinophosphonium hexafluorophosphate, or the like in an organic solvent, for example methylene chloride or preferably, N,N-dimethylformamide or the like followed by addition of aqueous ammonium hydroxide or preferably, ammonia. The reaction is carried out using organic base for example triethylamine, diisopropylethylamine or the like. Any conditions conventionally used in synthesizing acetamide can be utilized to carry out the reaction of step (a).

The compound of formula III is the compound of formula I where $R^3$ and $R^4$ are hydrogens.

The compound of formula I where $R^3$ is —$(CH_2)_g$OH wherein g is 0 and $R^4$ is hydrogen, can be prepared via reaction step (b) by first converting acid to an acid halide. The reaction can be carried out using halogenating reagent for example, thionyl chloride or preferable, oxalyl chloride, or the like. Any conditions conventionally used in converting acid to an acid halide can be utilized to carry out the reaction of step (b). The acid halide can be reacted with hydroxylamine hydrochloride in solvent, for example ethanol, tetrahydrofuran, or, preferably, tetrahydrofuran (5): water (1) or the like. The reaction is carried out utilizing base for example potassium hydroxide, or preferably, triethylamine or the like. Any conditions conventional for the synthesis of hydroxamic acids can be utilized to carry out the reaction of step (b).

The compound of formula IV is the compound of formula I where $R^3$ is —$(CH_2)_g$OH wherein g is 0 and $R^4$ is hydrogen.

The compound of formula I where $R^3$ is —$(CH_2)_g$OH wherein g is 1 or 2 and $R^4$ is hydrogen, methyl or ethyl can be prepared via reaction step (c) by reacting the compound of formula II with $NHR^3R^4$ (VI) by utilizing coupling reagent for example, 1-[3-(Dimethylamino)propyl]-3-ethylcarbodiimide hydrochloride (EDC) or the like. The reaction can be carried out using condensation-enhancing reagent for example, hydroxy benzotriazole. The reaction can be carried out in suitable solvent for example, methylene chloride, N,N-dimethylformamide or the like, preferably at a temperature from 0° C. to the reflux temperature. The compounds of formula VI are commercially available.

The compound of formula V is the compound of formula I where $R^3$ is hydrogen or —$(CH_2)_g$OH wherein g is 0, 1 or 2 and $R^4$ is methyl or ethyl.

Reaction Scheme 1

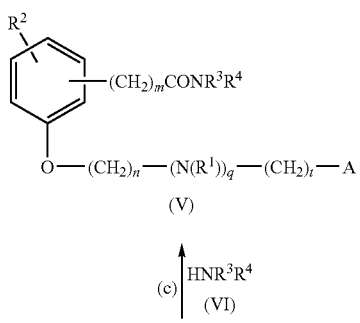

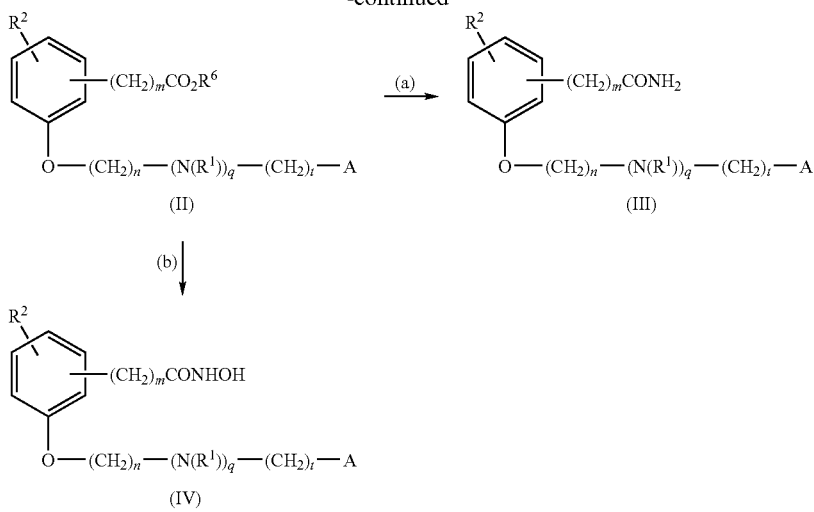

The compound of formula II where m is 0 to 2, q is 0, t is 0 or 1, and n is 1 or 2, $R^2$ is hydrogen, halo, alkoxy having from 1 to 3 carbon atoms or alkyl having from 1 to 3 carbon atoms, and $R^6$ is hydrogen, i.e. compounds of formula:

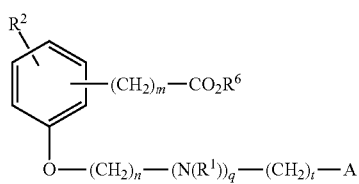

wherein A is described as above, can be prepared from the compound of the formula,

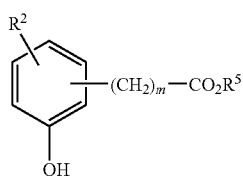

via reaction scheme 2.

In the reaction scheme 2, A, t, n, m, $R^2$ and $R^6$ are as above. $R^5$ is an alkyl group having 1 to 2 carbon atoms, and Y is a leaving group.

The compound of formula VII can be converted to the compound of formula II via reaction of step (d) using Mitsunobu condensation of compound of formula VII with compound of formula VIII using triphenylphosphine and diethyl azodicarboxylate or diisopropyl azodicarboxylate. The reaction can be carried out in a suitable solvent for example tetrahydrofuran. Any of the conditions conventionally used in Mitsunobu reactions can be utilized to carry out the reaction of step (d).

The compound of formula II can also be prepared by etherifying or alkylating the compound of formula VII with the compound of formula IX as in reaction of step (e). In the compound of formula IX, Y, include but are not limited to mesyloxy, tosyloxy, chloro, bromo, iodo, and the like. Any conventional method of etherifying of a hydroxyl group by reaction with a leaving group can be utilized to carry out the reaction of step (e).

The compound of formula II where $R^5$ is alkyl group having 1 to 2 carbon atoms. The compound of formula II can be converted to the free acid i.e. the compound of formula II where $R^6$ is H by ester hydrolysis. Any conventional method of ester hydrolysis will produce the compound of formula II where $R^6$ is H.

Reaction Scheme 2

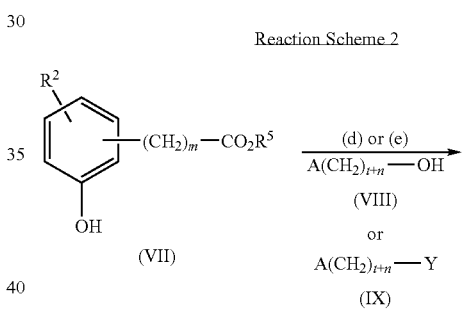

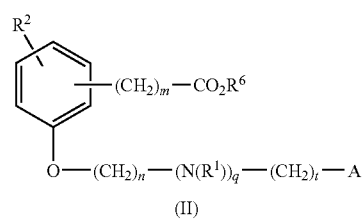

The compound of formula II where m is 3, q is 0, t is 0 or 1, and n is 1 or 2, $R^2$ is hydrogen, halo, alkoxy having from 1 to 3 carbon atoms or alkyl having from 1 to 3 carbon atoms, and $R^6$ is hydrogen, i.e. compounds of formula:

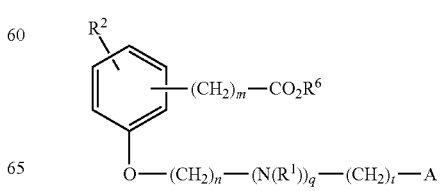

wherein A is described as above, can be prepared from the compound of the formula,

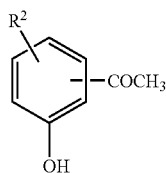

via reaction of scheme 3.

In the reaction scheme of Scheme 3, A, t, n, m, $R^6$ and $R^2$ are as above. $R^5$ is an alkyl group having from 1 to 2 carbon atoms, and Y is a leaving group.

The compound of formula X can be converted to the compound of formula XI via reaction step (f) in the same manner as described in connection with step (d) of reaction scheme 2.

The compound of formula XI can also be prepared in the same manner via reaction step (g) as described in connection with step (e) of reaction scheme 2.

The reaction of step (g) is preferred over step (f) if compound of formula IX is readily available.

The compound of formula XI can be converted to the compound of formula XIII via reaction of step (h) by alkylating the compound of formula XI with the compound of formula XII. This reaction can be carried out in the presence of approximately a molar equivalent of a conventional base that converts acetophenone to 3-keto ester (i.e. gamma-keto ester). In carrying out this reaction it is generally preferred but not limited to utilize alkali metal salts of hexamethyldisilane such as lithium bis-(trimethylsilyl)amide and the like. Generally this reaction is carried out in inert solvents such as tetrahydrofuran: 1,3-Dimethyl-3,4,5,6-tetrahydro-2(1H)-pyrimidinone. Generally the reaction is carried out at temperatures of from −65° C. to 25° C. Any of the conditions conventional in such alkylation reactions can be utilized to carry out the reaction of step (h).

The compound of formula XIII can be converted to the free acid by ester hydrolysis. Any conventional method of ester hydrolysis will produce the compound of formula XIII where $R^6$ is H.

The compound of formula XIII can be converted to the compound of II via reaction step (i) by reducing the ketone group to $CH_2$ group. The reaction can be carried out by heating compound of formula XIII with hydrazine hydrate in the presence of a base such as KOH or NaOH in suitable solvent such as ethylene glycol. In carrying out this reaction it is generally preferred but not limited to utilize KOH as base. Any of the conditions conventionally used in Wolff-Kishner reduction reactions can be utilized to carry out the reaction of step (i).

Reaction Scheme 3

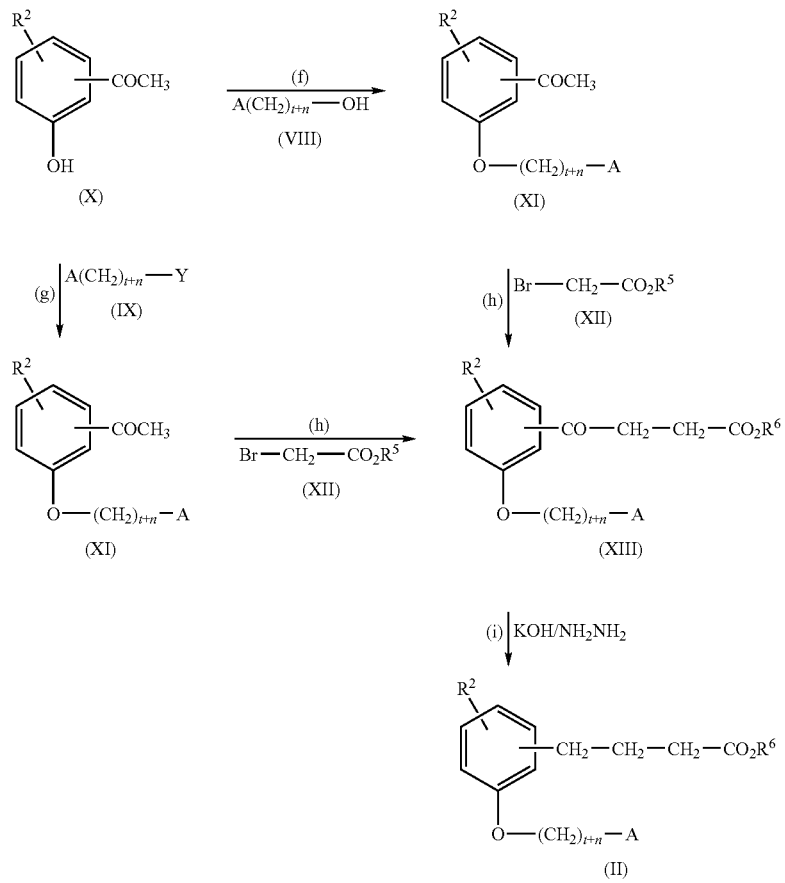

The compound of formula II where m is 3, q is 1, t is 0 or 1, and n is 1 or 2, $R^1$ is an alkyl having 1 to 3 carbon atoms, $R^2$ is hydrogen, halo, alkoxy having from 1 to 3 carbon atoms or alkyl having from 1 to 3 carbon atoms, and $R^6$ is hydrogen, i.e. compounds of formula:

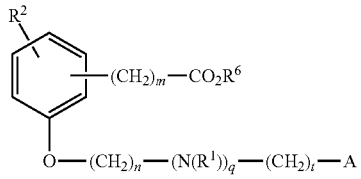

wherein A is described as above, can be prepared from the compound of the formula,

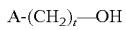

via reaction of scheme 4.

In the reaction scheme of Scheme 4, t, n, A, $R^1$, $R^2$, and $R^6$ are as above. $R^5$ is an alkyl group having from 1 to 2 carbon atoms. Y is chloro or bromo.

The compound of formula XIV can be mesylated to furnish the compound of formula XV via reaction of step (j). Any conventional conditions to carry out the mesylation reaction of a hydroxyl group can be utilized to carry out the step (j). The compound of formula XV is then heated with the compound of formula XVI to produce the compound of formula XVII. Any of the conditions conventional to produce amino alcohol can be utilized to carry out the reaction of step (k).

In the compound of formula XVII, alcohol can be displaced by chloro or bromo by treating the compound of formula XVII with thionyl chloride, bromine, or phosphorus tribromide or the like to produce the compound of formula XVIII. Any conventional method to displace alcohol with chloro or bromo can be utilized to carry out the reaction of step (l).

The compound of formula XVIII can be reacted with the compound of formula X via reaction of step (m) in the presence of a suitable base such as potassium carbonate, sodium hydride, triethylamine and the like. The reaction can be carried out in conventional organic solvents such as dimethylformamide, tetrahydrofuran and the like to produce the corresponding compound of formula XIX. Any conventional method of etherification of a hydroxyl group in the presence of base (preferred base being potassium carbonate) with chloro or bromo can be utilized to carry out the reaction of step (m).

The compound of formula XIX can be converted to the compound of formula XX via reaction of step (n) by alkylating the compound of formula XIX with the compound of formula XII. This reaction is carried out in the presence of approximately a molar equivalent of a suitable base such as lithium hexamethyldisilane. This reaction is carried out in the same manner as described in connection with the reaction of step (h) of Scheme 3.

The compound of formula XX can be converted to the free acid by ester hydrolysis. Any conventional method of ester hydrolysis will produce the compound of formula XX where $R^6$ is H.

The compound of formula XX can be converted to the compound of II via reaction of step (o) by reducing the ketone group to $CH_2$ group. The reaction can be carried out by heating compound of formula XX with hydrazine hydrate and base such as KOH or NaOH in suitable solvent such as ethylene glycol. In carrying out this reaction it is generally preferred but not limited to utilize KOH as base. Any of the conditions conventionally used in Wolff-Kishner reduction reactions can be utilized to carry out the reaction of step (o).

Reaction Scheme 4

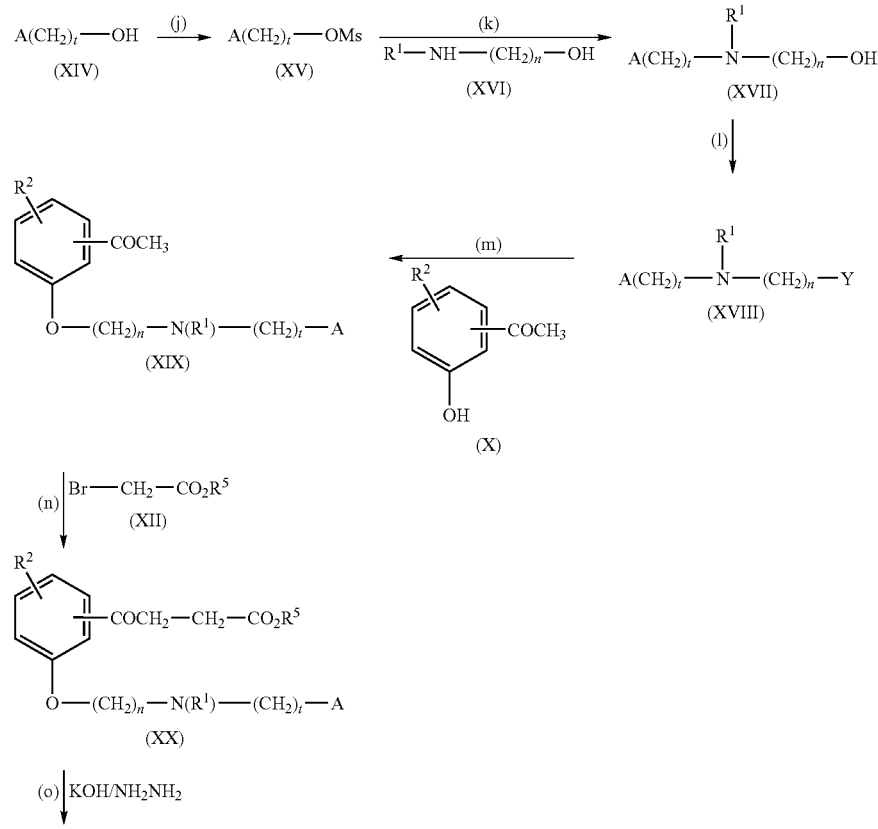

-continued

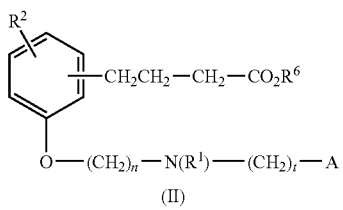
(II)

The compound of formula II where m is 0 to 2, q is 1, t is 0 or 1, and n is 1 or 2, $R^1$ is an alkyl having 1 to 3 carbon atoms, $R^2$ is hydrogen, halo, alkoxy having from 1 to 3 carbon atoms or alkyl having from 1 to 3 carbon atoms, and $R^6$ is hydrogen, i.e. compounds of formula:

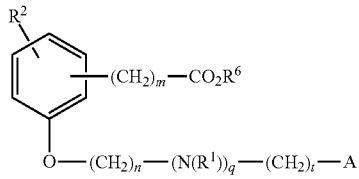

wherein A is described as above, can be prepared from the compound of the formula,

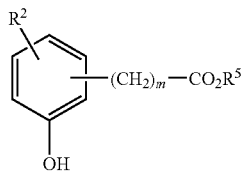

via reaction scheme 5.

In the reaction scheme 5, A, t, n, m, $R^1$, $R^2$ and $R^6$ are as above. $R^5$ is an alkyl group having 1 to 2 carbon atoms, and Y is a leaving group.

The compound of formula VII can be converted to the compound of formula II via reaction step (p) by treating the compound of formula VII with the compound of formula XVII. This reaction is carried out in the same manner as described in connection with the reaction of step (d) of Scheme 2.

The compound of formula VII can also be converted to the compound of formula II via reaction step (q) by treating the compound of formula VII with the compound of formula XVIII. This reaction is carried out in the same manner as described in connection with the reaction of step (e) of Scheme 2.

The compound of formula II can be converted to the free acid i.e. the compound of formula II where $R^6$ is H by ester hydrolysis. Any conventional method of ester hydrolysis will produce the compound of formula II where $R^6$ is H.

Reaction Scheme 5

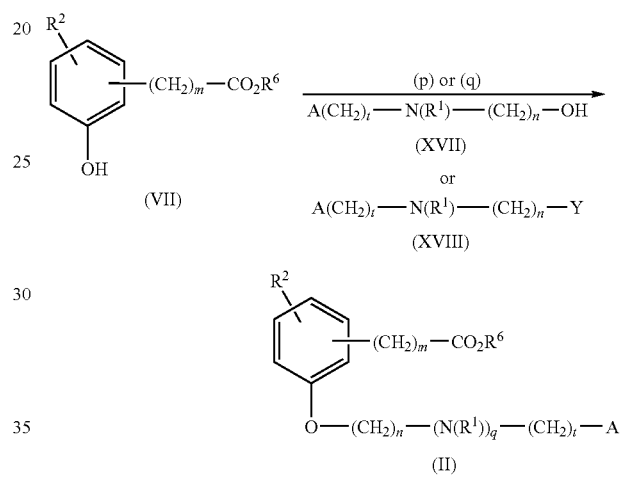

The compound of formula II where m is 4 or 5, q is 0 or 1, t is 0 or 1, and n is 1 or 2, $R^1$ is an alkyl having 1 to 3 carbon atoms, $R^2$ is hydrogen, halo, alkoxy having from 1 to 3 carbon atoms or alkyl having from 1 to 3 carbon atoms, and $R^6$ is hydrogen, i.e. compounds of formula:

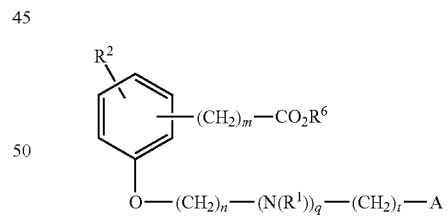

wherein A is described as above, can be prepared from the compound of the formula,

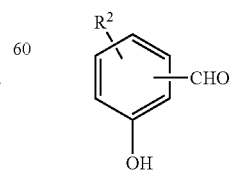

via reaction of scheme 6.

In the reaction scheme of Scheme 6, A, t, n, q, $R^1$ and $R^2$ are as above. $R^5$ is an alkyl group having from 1 to 2 carbon atoms, p is 3 or 4, and s is 2 or 3. Y is a halide or leaving group.

The compound of formula XXI can be converted to the compound of formula XXII via reaction step (r) by treating the compound of formula XXI with the compound of formula VIII or XVII in the same manner as described in connection with step (d) of reaction scheme 2.

The compound of formula XXII can also be prepared via reaction step (s) by treating the compound of formula XXI with the compound of formula IX or XVIII in the same manner as described in connection with step (e) of reaction scheme 2.

The reaction of step (s) is preferred over step (r).

The compound of formula XXII can be converted to the compound of formula XXIV via reaction of step (t) using Wittig reaction by treating the compound of formula XXII with the compound of formula XXIII. Any conventional method of reacting an aldehyde with a triarylphosphine hydrohalide can be utilized to carry out the reaction of step (t). Any of the conditions conventional in Wittig reactions can be utilized to carry out the reaction of step (t). The product can be isolated and purified by techniques such as extraction, evaporation, chromatography, and recrystallization.

The compound of formula XXIV can be converted to the compound of formula II via reaction step (u) by hydrogenation. Any conventional method of hydrogenation can be utilized to carry out this reaction. The method of hydrogenation include but not limited to by treating the compound of formula XXIV, in an inert degassed solvent for example benzene:ethanol (1:1), with hydrogen gas in the presence of a catalyst for example tris(triphenylphosphine)chlororhodium (1) (Wilkinson's catalyst). Any conditions conventional in catalytic hydrogenation can be utilized to carry out the reaction step (u).

The compound of formula XXV can be converted to the compound of formula II by ester hydrolysis. Any conventional method of ester hydrolysis will produce the compound of formula II where $R^6$ is H.

Reaction Scheme 6

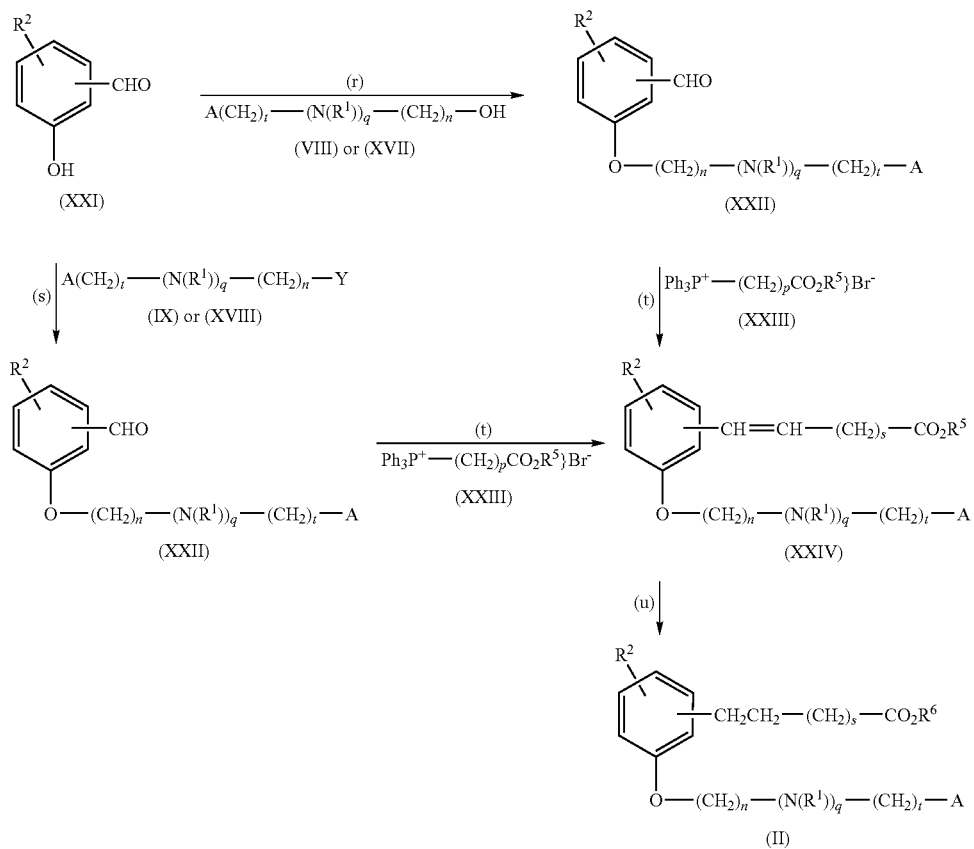

The compound of formula $A(CH_2)_{t+n}$—OH (VIII), and the compound of formula $A(CH_2)_{t+n}$—Y (IX) wherein Y is a leaving group and A is described as above, can be prepared via reaction of scheme 7.

In the reaction of Scheme 7, A and Y are described as above.

The compound of formula XXV can be reduced to the compound of formula XXVI via reaction of step (v). The reaction is carried out utilizing a conventional reducing agent for example alkali metal hydride such as lithium aluminum hydride. The reaction is carried out in a suitable solvent, such as tetrahydrofuran. Any of the conditions conventional in such reduction reactions can be utilized to carry out the reaction of step (v).

The compound of formula XXVI is the compound of formula VIII where t is 0 and n is 1.

The compound of formula XXVI can be converted to the compound of formula XXVII by displacing hydroxyl group with a halogen group preferred halogen being bromo or chloro. Appropriate halogenating reagents include but are not limited to thionyl chloride, bromine, phosphorous tribromide, carbon tetrabromide and the like. Any conditions conventional in such halogenation reactions can be utilized to carry out the reaction of step (w).

The compound of formula XXVII is the compound of formula IX where t is 0 and n is 1.

The compound of formula XXVII can be converted to the compound of formula XXVIII by reacting XXVII with an alkali metal cyanide for example sodium or potassium cyanide. The reaction is carried out in a suitable solvent, such as dimethyl sulfoxide. Any of the conditions conventionally used in the preparation of nitrite can be utilized to carry out the reaction of step (x).

The compound of formula XXVIII can be converted to the compound of formula XXIX via reaction step (y) by acid or base hydrolysis. In carrying out this reaction it is generally preferred to utilize basic hydrolysis, for example aqueous sodium hydroxide. Any of the conditions conventionally used in hydrolysis of nitrite can be utilized to carry out the reaction of step (y).

The compound of formula XXIX can be reduced to give the compound of formula XXX via reaction of step (z). This reaction can be carried out in the same manner as described hereinbefore in the reaction of step (v).

The compound of formula XXX is the compound of formula VIII where t is 1 and n is 1.

The compound of formula XXX can be converted to the compound of formula XXXI via reaction of step (a') in the same manner as described hereinbefore in connection with the reaction of step (w).

The compound of formula XXXI is the compound of formula IX where t is 1 and n is 1.

The compound of formula XXXI can be reacted with diethyl malonate utilizing a suitable base for example sodium hydride to give compound of formula XXXII. The reaction is carried out in suitable solvents, such as dimethylformamide, tetrahydrofuran and the like. Any of the conditions conventional in such alkylation reactions can be utilized to carry out the reaction of step (b').

The compound of formula XXXII can be hydrolyzed by acid or base to give compound of formula XXXVIII via reaction of step (c').

The compound of formula XXXIII can be converted to the compound of formula XXXIV via reaction of step (d') in the same manner as described hereinbefore in connection with the reaction of step (v).

The compound of formula XIV is the compound of formula VIII where t is 1 and n is 2.

The compound of formula XXXIV can be converted to the compound of formula XXXV via reaction of step (e') in the same manner as described hereinbefore in connection with the reaction of step (w).

The compound of formula XXXV is the compound of formula IX where t is 1 and n is 2.

Reaction Scheme 7

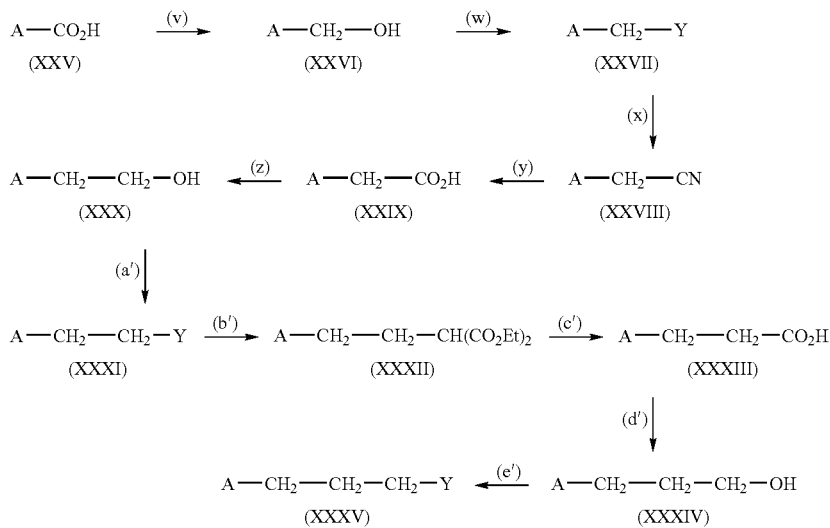

The compound of formula VII, where m is 0 to 2, $R^5$ is an alkyl group having from 1 to 2 carbon atoms and $R^2$ is hydrogen, halo, alkoxy having from 1 to 3 carbon atoms or alkyl having from 1 to 3 carbon atoms, i.e. compounds of formula:

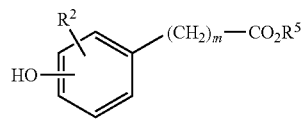

can be prepared via reaction of scheme 8.

In the reaction of Scheme 8, $R^6$ is H. $R^2$ and $R^5$ is as above.

The compound of formula II can be converted to the compound of formula VII via reaction of step (f') by esterification of compound of formula II with methanol or ethanol. The reaction can be carried out either by using catalysts for example $H_2SO_4$, TsOH and the like or by using dehydrating agents for example dicyclohexylcarbodiimide and the like. Any of the conditions conventional in such esterification reactions can be utilized to carry out the reaction of step (f').

Reaction Scheme 8

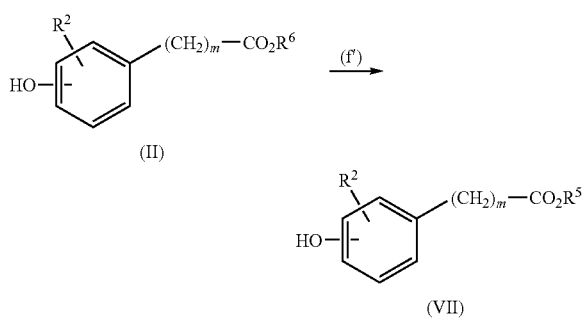

The compound of formula X where $R^2$ is hydrogen, halo, alkoxy having from 1 to 3 carbon atoms or alkyl having from 1 to 3 carbon atoms, i.e. compounds of formula:

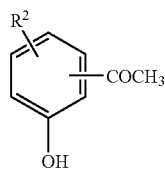

can be prepared via reaction of scheme 9.

In the reaction of Scheme 9, m is 0 and $R^6$ is H and $R^2$ is hydrogen, halo, alkoxy having from 1 to 3 carbon atoms or alkyl having from 1 to 3 carbon atoms.

The compound of formula X can be synthesized according to the method of George M Rubottom et al., J. Org. Chem. 1983, 48, 1550-1552.

Reaction Scheme 9

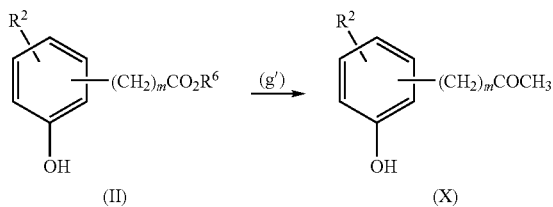

The compound of formula VII where m is 1 to 2, $R^5$ is an alkyl group having from 1 to 2 carbon atoms and $R^2$ is hydrogen, halo, alkoxy having from 1 to 3 carbon atoms or alkyl having from 1 to 3 carbon atoms, i.e. compounds of formula:

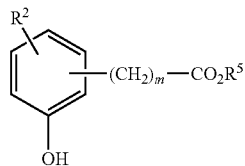

can be prepared via reaction of scheme 10.

In the reaction of Scheme 10, $R^2$ and $R^5$ are as above. $R^7$ is a hydroxy protecting group.

The compound of formula VII where m is 0 can be converted to the compound of formula XXXVI via reaction of step (h') by protecting the hydroxy group by utilizing suitable protecting groups such as those described in Protecting Groups in Organic Synthesis by T. Greene.

The compound of formula XVI can be reduced to the compound of formula XXXVII by utilizing conventional reducing reagent that converts acid to an alcohol via reaction of step (i'). In carrying out this reaction, it is generally preferred but not limited to utilize lithium aluminum hydride. The reaction is carried out in a suitable solvent such as tetrahydrofuran and the like. Any of the conditions conventional in such reduction reactions can be utilized to carry out the reaction of step (i').

The compound of formula XXXVII can be converted to the compound of formula XXXVIII by displacing hydroxy group with a halogen preferred halogen being bromo or chloro. Appropriate halogenating reagents include but are not limited to thionyl chloride, bromine, phosphorous tribromide, carbon tetrabromide and the like. Any conditions conventional in such halogenation reactions can be utilized to carry out the reaction of step (j').

The compound of formula XXXVIII can be converted to the compound of formula XXXIX by reacting XXXVIII with an alkali metal cyanide for example sodium or potassium cyanide. The reaction is carried out in a suitable solvent such as dimethyl sulfoxide. Any of the conditions conventionally used in the preparation of nitrites can be utilized to carry out the reaction of step (k').

The compound of formula XXXIX can be converted to the compound of formula XL via reaction step (l') by acid or base hydrolysis. In carrying out this reaction, it is generally preferred to utilize basic hydrolysis, for example aqueous sodium hydroxide. Any of the conditions conventional for the hydrolysis of nitrile can be utilized to carry out the reaction of step (l').

The compound of formula XL can be converted to the compound of formula XLI via reaction of step (m') by removal of hydroxy protecting group utilizing suitable deprotecting reagents such as those described in Protecting Groups in Organic Synthesis by T. Greene.

The compound of formula XLI can be converted to compound of formula VII where m is 1 and $R^5$ is an alkyl group having from 1 or 2 carbon atoms by esterification of compound of formula XLI with methanol or ethanol. The reaction can be carried out either by using catalysts for example $H_2SO_4$, TsOH and the like or by using dehydrating agents for example dicyclohexylcarbodiimide and the like. Any of the conditions conventional in such esterification reactions can be utilized to carry out the reaction.

The compound of formula XXXVIII can be reacted with diethyl malonate utilizing a suitable base for example sodium hydride to give compound of formula XLII. The reaction is carried out in suitable solvents, such as dimethylformamide, tetrahydrofuran and the like. Any of the conditions conventional in such alkylation reactions can be utilized to carry out the reaction of step (n').

The compound of formula XLII can be hydrolyzed by acid or base and removal of hydroxy protecting group utilizing suitable deprotecting reagents such as those described in Protecting Groups in Organic Synthesis by T. Greene to give compound of formula XLIII via reaction of step (o').

The compound of formula XLIII can be converted to the compound of formula VII where m is 2 and $R^5$ is an alkyl group having from 1 or 2 carbon atoms by esterification of compound of formula XLIII with methanol or ethanol. The reaction can be carried out either by using catalysts for example $H_2SO_4$, TsOH and the like or by using dehydrating agents for example dicyclohexylcarbodiimide and the like. Any of the conditions conventional in such esterification reactions can be utilized to carry out the reaction.

Reaction Scheme 10

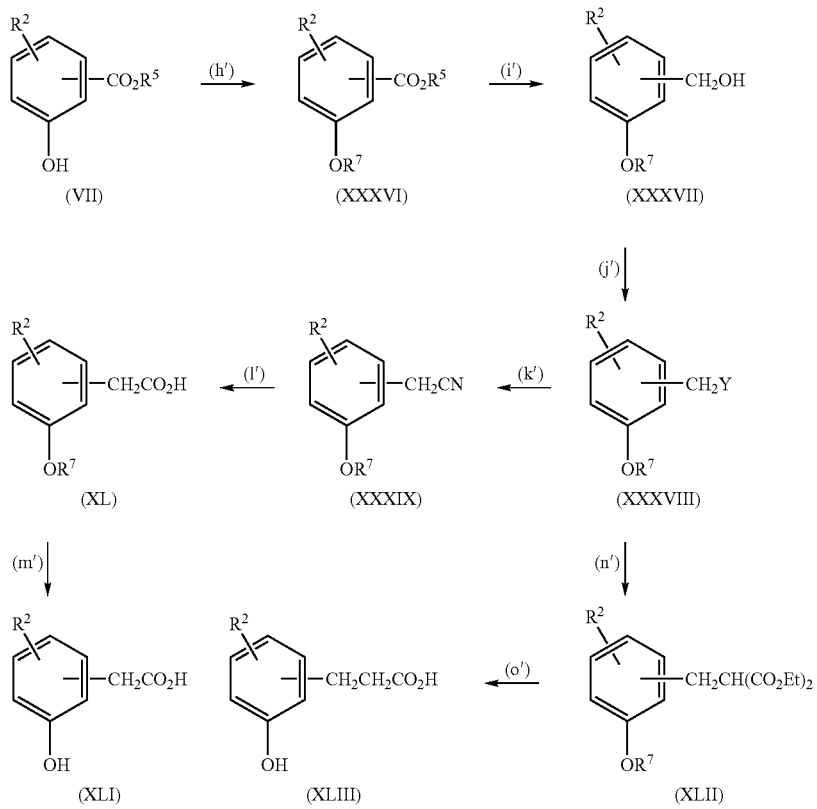

The compound of formula XXI where $R^2$ is hydrogen, halo, alkoxy having from 1 to 3 carbon atoms or alkyl having from 1 to 3 carbon atoms, i.e. compounds of formula:

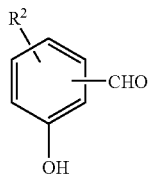

can be prepared via reaction of scheme 11.

In the reaction scheme of Scheme 11, $R^2$ is as above. $R^7$ is a protecting group.

The compound of formula XXXVII can be converted to the compound of formula XLIV via reaction of step (p') by oxidation of alcohol to an aldehyde. The reaction can be carried out utilizing a suitable oxidizing agent for example pyridinium chlorochromate, dimethyl sulfoxide activated by 2,4,6-trichloro[1,3,5]-triazine (cyanuric chloride, TCT) under Swern oxidation conditions (J.O.C. 2001, 66, 7907-7909) or the like. Any of the conditions conventional in such oxidation reactions can be utilized to carry out the reaction of step (p').

In the compound of formula XLIV, the hydroxy group can be deprotected via reaction of step (q') by utilizing suitable deprotecting reagents such as those described in Protecting Groups in Organic Synthesis by T. Greene to give the compound of formula XXI.

Reaction Scheme 11

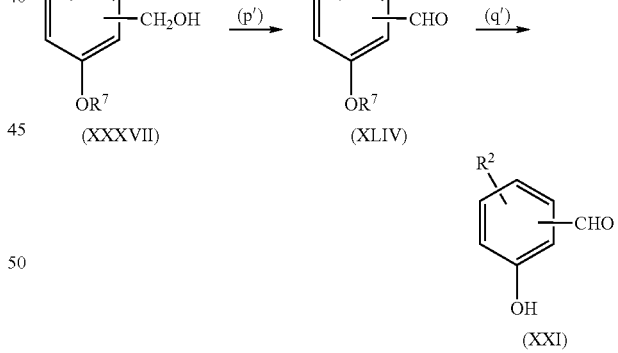

The compound of formula XXIII, where $R^5$ is an alkyl group having from 1 to 2 carbon atoms and p is 3 or 4, i.e. compounds of formula:

$$Ph_3P^+\text{—}(CH_2)_p CO_2R^5\}Br^-$$

can be prepared via reaction of scheme 12.

In the reaction scheme of Scheme 12, $R^5$ and p are as above.

The compound of formula XLV can be reacted with the compound of formula XLVI via the reaction of step (r') to give compound of formula XXIII. Any of the conditions conventionally used in reacting triphenylphosphine with hydrohalide can be utilized to carry out the reaction of step (r').

Reaction Scheme 12

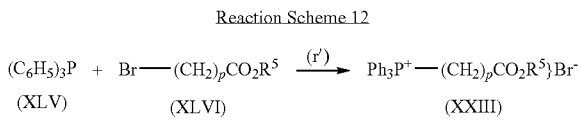

The compound of formula II, where m is 0, $R^6$ is H and $R^2$ is halo, i.e. compounds of formula:

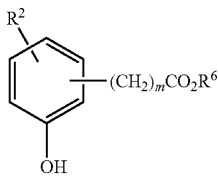

are either commercially available or can be prepared according to the methods described in the literature as follows:
1. 3-Br or F-2-$OHC_6H_3CO_2H$
Canadian Journal of Chemistry (2001), 79(11) 1541-1545.
2. 4-Br-2-$OHC_6H_3CO_2H$
WO 9916747 or JP 04154773.
3. 2-Br-6-$OHC_6H_3CO_2H$
JP 47039101.
4. 2-Br-3-$OHC_6H_3CO_2H$
WO 9628423.
5. 4-Br-3-$OHC_6H_3CO_2H$
WO 2001002388.
6. 3-Br-5-$OHC_6H_3CO_2H$
Journal of labeled Compounds and Radiopharmaceuticals (1992), 31 (3), 175-82.
7. 2-Br-5-$OHC_6H_3CO_2H$ and 3-Cl-4-$OHC_6H_3CO_2H$
WO 9405153 and U.S. Pat. No. 5,519,133.
8. 2-Br-4-$OHC_6H_3CO_2H$ and 3-Br-4-$OHC_6H_3CO_2H$
WO 20022018323
9. 2-Cl-6-$OHC_6H_3CO_2H$
JP 06293700
10. 2-Cl-3-$OHC_6H_3CO_2H$
Proceedings of the Indiana Academy of Science (1983), Volume date 1982, 92, 145-51.
11. 3-Cl-5-$OHC_6H_3CO_2H$
WO 2002000633 and WO 2002044145.
12. 2-Cl-5-$OHC_6H_3CO_2H$
WO 9745400.
13. 5-I-2-$OHC_6H_3CO_2H$ and 3-I, 2-$OHC_6H_3CO_2H$
Z. Chem. (1976), 16(8), 319-320.
14. 4-I-2-$OHC_6H_3CO_2H$
Journal of Chemical Research, Synopses (1994), (11), 405.
15. 6-I-2-$OHC_6H_3CO_2H$
U.S. Pat. No. 4,932,999.
16. 2-I-3-$OHC_6H_3CO_2H$ and 4-I-3-$OHC_6H_3CO_2H$
WO 9912928.
17. 5-I-3-$OHC_6H_3CO_2H$
J. Med. Chem. (1973), 16(6), 684-7.
18. 2-I-4-$OHC_6H_3CO_2H$
Collection of Czechoslovak Chemical Communications, (1991), 56(2), 459-77.
19. 3-I-4-$OHC_6H_3CO_2$,
J.O.C. (1990), 55(18), 5287-91.

The compound of formula II, where m is 0, $R^6$ is H and $R^2$ is alkoxy having from 1 to 3 carbon atoms, i.e. compounds of formula:

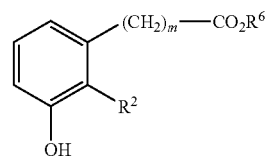

can be synthesized via the reaction of scheme 13.

In the reaction of Scheme 13, $R^6$ and $R^2$ are as above, and $R^5$ is an alkyl group having from 1 to 2 carbon atoms.

The compound of formula XLVII can be converted to the compound of formula XLVIII by reducing aldehyde to primary alcohol. In carrying out this reaction, it is preferred but not limited to use sodium borohydride as the reducing reagent. Any of the conditions suitable in such reduction reactions can be utilized to carry out the reaction of step (s').

The compound of formula XLVIII can be converted to the compound of formula XLIX via reaction of step (t') by protecting 1-3 Diols by using 1,1,3,3-Tetraisopropyldisiloxane. The suitable conditions for this protecting group can be described in the Protecting Groups in Organic Synthesis by T. Greene.

The compound of formula XLIX can be converted to the compound of formula L via reaction of step (u') by protecting phenol group by using benzyl bromide. The suitable conditions for this protecting group can be described in the Protecting Groups in Organic Synthesis by T. Greene.

The compound of formula L can be converted to the compound of formula LI by deprotection using tetrabutylammonium fluoride via reaction of step (v'). The suitable conditions for the deprotection can be described in the Protecting Groups in Organic Synthesis by T. Greene.

The compound of formula LI can be converted to compound of formula LII via reaction of step (w') by oxidation. Any conventional oxidizing group that converts primary alcohol to an acid for example chromium oxide and the like can be utilized to carry out the reaction of step (w').

The compound of formula LII can be converted to the compound of formula LIII by esterification of compound of formula LII with methanol or ethanol. The reaction can be carried out either by using catalysts for example $H_2SO_4$, TsOH and the like or by using dehydrating agents for example dicyclohexylcarbodiimide and the like. Any of the conditions conventional in such esterification reactions can be utilized to carry out the reaction of step (x').

The compound of formula LIII can be converted to the compound of formula LIV by etherifying or alkylating the compound of formula LIII with methyl halide or ethyl halide or propyl halide by using suitable base for example potassium carbonate, sodium hydride and the like. The reaction is carried out in conventional solvents, such as tetrahydrofuran, dimethylformamide. The reaction is generally carried out at temperatures of from 0° C. to 40° C. Any of the conditions suitable in such alkylation reactions can be utilized to carry out the reaction of step (y').

The compound of formula LIV can be converted to the compound of formula LV via reaction step (z') by deprotection of ester and benzyl groups. The suitable deprotecting conditions can be described in the Protecting Groups in Organic Synthesis by T. Greene.

Reaction Scheme 13

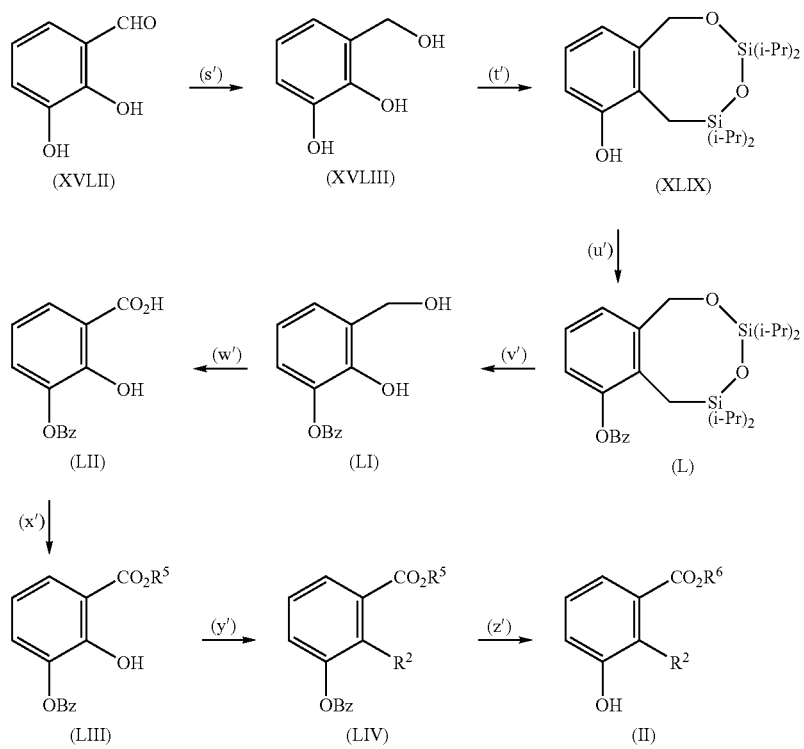

The compound of formula II, where m is 0, $R^6$ is H and $R^2$ is an alkoxy having from 1 to 3 carbon atoms, i.e. compounds of formula:

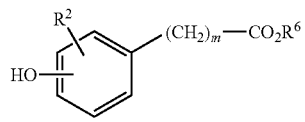

are either commercially available or can be prepared according to the methods described in the literature as follows:
1. 2-OMe-4-OHC$_6$H$_3$CO$_2$H.
  US 2001034343 or WO 9725992.
2. 5-OMe-3-OHC$_6$H$_3$CO$_2$H
  J.O.C (2001), 66(23), 7883-88.
3. 2-OMe-5-OHC$_6$H$_3$CO$_2$H
  U.S. Pat. No. 6,194,406 (Page 96) and Journal of the American Chemical Society (1985), 107(8), 2571-3.
4. 3-OEt-5-OHC$_6$H$_3$CO$_2$H
  Taiwan Kexue (1996), 49(1), 51-56.
5. 4-OEt-3-OHC$_6$H$_3$CO$_2$H
  WO 9626176
6. 2-OEt-4-OHC$_6$H$_3$CO$_2$H
  Takeda Kenkyusho Nempo (1965), 24, 221-8.
  JP 07070025.
7. 3-OEt-4-OHC$_6$H$_3$CO$_2$H
  WO 9626176.
8. 3-OPr-2-OHC$_6$H$_3$CO$_2$H
  JP 07206658, DE 2749518.
9. 4-OPr-2-OHC$_6$H$_3$CO$_2$H
  Farmacia (Bucharest) (1970), 18(8), 461-6.
  JP 08119959.
10. 2-OPr-5-OHC$_6$H$_3$CO$_2$H and 2-OEt-5-OHC$_6$H$_3$CO$_2$H
  Adapt synthesis from U.S. Pat. No. 6,194,406 (Page 96) by using propyl iodide and ethyl iodide.
11. 4-OPr-3-OHC$_6$H$_3$CO$_2$H
  Adapt synthesis from WO 9626176
12. 2-OPr-4-OHC$_6$H$_3$CO$_2$H
  Adapt synthesis from Takeda Kenkyusho Nempo (1965), 24, 221-8 by using propyl halide.
13. 4-OEt-3-OHC$_6$H$_3$CO$_2$H
  Biomedical Mass Spectrometry (1985), 12(4), 163-9.
14. 3-OPr-5-OHC$_6$H$_3$CO$_2$H
  Adapt synthesis from Taiwan Kexue (1996), 49(1), 51-56 by using propyl halide.

The compound of formula II, where m is 0, $R^6$ is H and $R^2$ is an alkyl having 1 to 3 carbon atoms, i.e. compounds of formula:

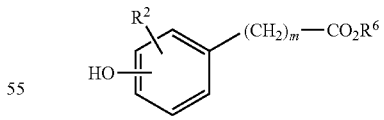

are either commercially available or can be prepared according to the methods described in the literature as follows:
1. 5-Me-3-OHC$_6$H$_3$CO$_2$H and 2-Me-5-OHC$_6$H$_3$CO$_2$H
  WO 9619437.
  J.O.C. 2001, 66, 7883-88.
2. 2-Me-4-OHC$_6$H$_3$CO$_2$H
  WO 8503701.
3. 3-Et-2-OHC$_6$H$_3$CO$_2$H and 5-Et-2-OHC$_6$H$_3$CO$_2$H
  J. Med. Chem. (1971), 14(3), 265.

4. 4-Et-2-OHC$_6$H$_3$CO$_2$H
Yaoxue Xuebao (1998), 33(1), 67-71.
5. 2-Et-6-OHC$_6$H$_3$CO$_2$H and 2-n-Pr-6-OHC$_6$H$_3$CO$_2$H
J. Chem. Soc., Perkin Trans 1 (1979), (8), 2069-78.
6. 2-Et-3-OHC$_6$H$_3$CO$_2$H
JP 10087489 and WO 9628423.
7. 4-Et-3-OHC$_6$H$_3$CO$_2$H
J.O.C. 2001, 66, 7883-88.
WO 9504046.
8. 2-Et-5-OHC$_6$H$_3$CO$_2$H
J.A.C.S (1974), 96(7), 2121-9.
9. 2-Et-4-OHC$_6$H$_3$CO$_2$H and 3-Et-4-OHC$_6$H$_3$CO$_2$H
JP 04282345.
10. 3-n-Pr-2-OHC$_6$H$_3$CO$_2$H
J.O.C (1991), 56(14), 4525-29.
11. 4-n-Pr-2-OHC$_6$H$_3$CO$_2$H
EP 279630.
12. 5-n-Pr-2-OHC$_6$H$_3$CO$_2$H
J. Med. Chem. (1981), 24(10), 1245-49.
13. 2-n-Pr-3-OHC$_6$H$_3$CO$_2$H
WO 9509843 and WO 9628423.
14. 4-n-Pr-3-OHC$_6$H$_3$CO$_2$H
WO 9504046.
15. 2-n-Pr-5-OHC$_6$H$_3$CO$_2$H
Synthesis can be adapted from J.A.C.S (1974), 96(7), 2121-9 by using ethyl alpha formylvalerate.
16. 3-n-Pr-4-OHC$_6$H$_3$CO$_2$H
Polymer (1991), 32(11) 2096-105.
17. 2-n-Pr-4-OHC$_6$H$_3$CO$_2$H
3-Propylphenol can be methylated to 3-Propylanisole, which was then formulated to 4-Methoxy-3-benzaldehyde. The aldehyde can be oxidized by Jone's reagent to give corresponding acid and deprotection of methyl group by BBr$_3$ will give the title compound.
18. 1. 3-Et-5-OHC$_6$H$_3$CO$_2$H and 3-Pr-n-5-OHC$_6$H$_3$CO$_2$H
Adapt synthesis from J.O.C. 2001, 66, 7883-88 by using 2-Ethylacrolein and 2-Propylacrolein.

Therapeutic Use

This invention provides a method for treating a mammalian subject with a condition selected from the group consisting of insulin resistance syndrome and diabetes (both primary essential diabetes such as Type I Diabetes or Type II Diabetes and secondary nonessential diabetes), comprising administering to the subject an amount of a compound or salt as described herein effective to treat the condition. In accordance with the method of this invention a symptom of diabetes or the chance of developing a symptom of diabetes, such as atherosclerosis, obesity, hypertension, hyperlipidemia, fatty liver disease, nephropathy, neuropathy, retinopathy, foot ulceration and cataracts, each such symptom being associated with diabetes, can be reduced. This invention also provides a method for treating hyperlipidemia comprising administering to the subject an amount of a compound or salt as described herein effective to treat the condition. As shown in the Examples, the compounds reduce serum triglycerides and free fatty acids in hyperlipidemic animals. This invention also provides a method for treating cachexia comprising administering to the subject an amount of a compound or salt as described herein effective to treat the cachexia. This invention also provides a method for treating obesity comprising administering to the subject an amount of a compound or salt as described herein effective to treat the condition. This invention also provides a method for treating a condition selected from atherosclerosis or arteriosclerosis comprising administering to the subject an amount of a compound or salt as described herein effective to treat the condition. The compounds and salts of this invention are effective to treat hyperlipidemia, fatty liver disease, cachexia, obesity, atherosclerosis or arteriosclerosis whether or not the subject has diabetes or insulin resistance syndrome. The compound or salt can be administered by any conventional route of systemic administration. Preferably the compound or salt is administered orally. Accordingly, it is preferred for the medicament to be formulated for oral administration. Other routes of administration that can be used in accordance with this invention include rectally, parenterally, by injection (e.g. intravenous, subcutaneous, intramuscular or intraperitoneal injection), or nasally.

Further embodiments of each of the uses and methods of treatment of this invention comprise administering any one of the embodiments of the compounds and salts described above. In the interest of avoiding unnecessary redundancy, each such compound or salt and group of compounds and salts is not being repeated, but they are incorporated into this description of uses and methods of treatment as if they were repeated.

Many of the diseases or disorders that are addressed by the compounds of the invention fall into two broad categories: Insulin resistance syndromes and consequences of chronic hyperglycemia. Dysregulation of fuel metabolism, especially insulin resistance, which can occur in the absence of diabetes (persistent hyperglycemia) per se, is associated with a variety of symptoms, including hyperlipidemia, atherosclerosis, obesity, essential hypertension, fatty liver disease (NASH; non-alcoholic steatohepatitis), and, especially in the context of cancer or systemic inflammatory disease, cachexia. Cachexia can also occur in the context of Type I Diabetes or late-stage Type II Diabetes. By improving tissue fuel metabolism, the compounds and salts of the invention are useful for preventing or ameliorating diseases and symptoms associated with insulin resistance, as is demonstrated in animals in the Examples. While a cluster of signs and symptoms associated with insulin resistance may coexist in an individual patient, it many cases only one symptom may dominate, due to individual differences in vulnerability of the many physiological systems affected by insulin resistance. Nonetheless, since insulin resistance is a major contributor to many disease conditions, drugs which address this cellular and molecular defect are useful for prevention or amelioration of virtually any symptom in any organ system that may be due to, or exacerbated by, insulin resistance.

When insulin resistance and concurrent inadequate insulin production by pancreatic islets are sufficiently severe, chronic hyperglycemia occurs, defining the onset of Type II diabetes mellitus (NIDDM). In addition to the metabolic disorders related to insulin resistance indicated above, disease symptoms secondary to hyperglycemia also occur in patients with NIDDM. These include nephropathy, peripheral neuropathy, retinopathy, microvascular disease, ulceration of the extremities, and consequences of nonenzymatic glycosylation of proteins, e.g. damage to collagen and other connective tissues. Attenuation of hyperglycemia reduces the rate of onset and severity of these consequences of diabetes. Because, as is demonstrated in the Examples, active compounds and salts and compositions of the invention help to reduce hyperglycemia in diabetes, they are useful for prevention and amelioration of complications of chronic hyperglycemia.

Both human and non-human mammalian subjects can be treated in accordance with the treatment method of this invention. The optimal dose of a particular active agent of the invention for a particular subject can be determined in the clinical setting by a skilled clinician. In the case of oral administration to a human for treatment of disorders related to insulin resistance, diabetes, hyperlipidemia, fatty liver disease, cachexia or obesity the agent is generally administered in a daily dose of from 1 mg to 400 mg, administered once or twice per day. In the case of oral administration to a mouse the agent is generally administered in a daily dose from 1 to 300 mg of the agent per kilogram of body weight. Active compounds and salts of the invention are used as monotherapy in diabetes or insulin resistance syndrome, or in combination with one or more other drugs with utility in these types of diseases, e.g. insulin releasing agents, prandial insulin releasers, biguanides, or insulin itself. Such additional drugs are administered in accord with standard clinical practice. In some cases, compounds and salts of the invention will improve the efficacy of other classes of drugs, permitting lower (and therefore less toxic) doses of such agents to be administered to patients with satisfactory therapeutic results. Established safe and effective dose ranges in humans for representative compounds are: metformin 500 to 2550 mg/day; glyburide 1.25 to 20 mg/day; GLUCOVANCE (combined formulation of metformin and glyburide) 1.25 to 20 mg/day glyburide and 250 to 2000 mg/day metformin; atorvastatin 10 to 80 mg/day; lovastatin 10 to 80 mg/day; pravastatin 10 to 40 mg/day; and simvastatin 5-80 mg/day; clofibrate 2000 mg/day; gemfibrozil 1200 to 2400 mg/day, rosiglitazone 4 to 8 mg/day; pioglitazone 15 to 45 mg/day; acarbose 75-300 mg/day; repaglinide 0.5 to 16 mg/day.

Type I Diabetes Mellitus: A patient with Type I diabetes manages their disease primarily by self-administration of one to several doses of insulin per day, with frequent monitoring blood glucose to permit appropriate adjustment of the dose and timing of insulin administration. Chronic hyperglycemia leads to complications such as nephropathy, neuropathy, retinopathy, foot ulceration, and early mortality; hypoglycemia due to excessive insulin dosing can cause cognitive dysfunction or unconsciousness. A patient with Type I diabetes is treated with 1 to 400 mg/day of a compound or salt of this invention, in tablet or capsule form either as a single or a divided dose. The anticipated effect will be a reduction in the dose or frequency of administration of insulin required to maintain blood glucose in a satisfactory range, and a reduced incidence and severity of hypoglycemic episodes. Clinical outcome is monitored by measurement of blood glucose and glycosylated hemoglobin (an index of adequacy of glycemic control integrated over a period of several months), as well as by reduced incidence and severity of typical complications of diabetes. A compound or salt of this invention can be administered in conjunction with islet transplantation to help maintain the anti-diabetic efficacy of the islet transplant.

Type II Diabetes Mellitus: A typical patient with Type II diabetes (NIDDM) manages their disease by programs of diet and exercise as well as by taking medications such as metformin, glyburide, repaglinide, rosiglitazone, or acarbose, all of which provide some improvement in glycemic control in some patients, but none of which are free of side effects or eventual treatment failure due to disease progression. Islet failure occurs over time in patients with NIDDM, necessitating insulin injections in a large fraction of patients. It is anticipated that daily treatment with a compound or salt of the invention (with or without additional classes of antidiabetic medication) will improve glycemic control, reduce the rate of islet failure, and reduce the incidence and severity of typical symptoms of diabetes. In addition, compounds and salts of the invention will reduce elevated serum triglycerides and fatty acids, thereby reducing the risk of cardiovascular disease, a major cause of death of diabetic patients. As is the case for all other therapeutic agents for diabetes, dose optimization is done in individual patients according to need, clinical effect, and susceptibility to side effects.

Hyperlipidemia: Elevated triglyceride and free fatty acid levels in blood affect a substantial fraction of the population and are an important risk factor for atherosclerosis and myocardial infarction. Compounds and salts of the invention are useful for reducing circulating triglycerides and free fatty acids in hyperlipidemic patients. Hyperlipidemic patients often also have elevated blood cholesterol levels, which also increase the risk of cardiovascular disease. Cholesterol-lowering drugs such as HMG-CoA reductase inhibitors ("statins") can be administered to hyperlipidemic patients in addition to compounds and salts of the invention, optionally incorporated into the same pharmaceutical composition.

Fatty Liver Disease: A substantial fraction of the population is affected by fatty liver disease, also known as nonalcoholic steatohepatitis (NASH); NASH is often associated with obesity and diabetes. Hepatic steatosis, the presence of droplets of triglycerides with hepatocytes, predisposes the liver to chronic inflammation (detected in biopsy samples as infiltration of inflammatory leukocytes), which can lead to fibrosis and cirrhosis. Fatty liver disease is generally detected by observation of elevated serum levels of liver-specific enzymes such as the transaminases ALT and AST, which serve as indices of hepatocyte injury, as well as by presentation of symptoms which include fatigue and pain in the region of the liver, though definitive diagnosis often requires a biopsy. The anticipated benefit is a reduction in liver inflammation and fat content, resulting in attenuation, halting, or reversal of the progression of NASH toward fibrosis and cirrhosis.

Pharmaceutical Compositions

This invention provides a pharmaceutical composition comprising a compound or salt as described herein and a pharmaceutically acceptable carrier. Further embodiments of the pharmaceutical composition of this invention comprise any one of the embodiments of the compounds and salts described above. In the interest of avoiding unnecessary redundancy, each such compound or salt and group of compounds and salts is not being repeated, but they are incorporated into this description of pharmaceutical compositions as if they were repeated.

Preferably the composition is adapted for oral administration, e.g. in the form of a tablet, coated tablet, dragee, hard or soft gelatin capsule, solution, emulsion or suspension. In general the oral composition will comprise from 1 mg to 400 mg of such compound or salt. It is convenient for the subject to swallow one or two tablets, coated tablets, dragees, or gelatin capsules per day. However the composition can also be adapted for administration by any other conventional means of systemic administration including rectally, e.g. in the form of suppositories, parenterally, e.g. in the form of injection solutions, or nasally.

The biologically active compounds can be processed with pharmaceutically inert, inorganic or organic carriers for the production of pharmaceutical compositions. Lactose, corn starch or derivatives thereof, talc, stearic acid or its salts and the like can be used, for example, as such carriers for tablets, coated tablets, dragees and hard gelatin capsules. Suitable carriers for soft gelatin capsules are, for example, vegetable oils, waxes, fats, semi-solid and liquid polyols and the like. Depending on the nature of the active ingredient no carriers are, however, usually required in the case of soft gelatin capsules, other than the soft gelatin itself. Suitable carriers for the production of solutions and syrups are, for example, water, polyols, glycerol, vegetable oils and the like. Suitable carriers for suppositories are, for example, natural or hardened oils, waxes, fats, semil-liquid or liquid polyols and the like.

The pharmaceutical compositions can, moreover, contain preservatives, solubilizers, stabilizers, wetting agents, emulsifiers, sweeteners, colorants, flavorants, salts for varying the osmotic pressure, buffers, coating agents or antioxidants. They can also contain still other therapeutically valuable substances, particularly antidiabetic or hypolipidemic agents that act through mechanisms other than those underlying the effects of the compounds of the invention. Agents which can advantageously be combined with compounds of the invention in a single formulation include but are not limited to biguanides such as metformin, insulin releasing agents such as the sulfonylurea insulin releaser glyburide and other sulfonylurea insulin releasers, cholesterol-lowering drugs such as the "statin" HMG-CoA reductase inhibitors such as atrovastatin, lovastatin, pravastatin and simvastatin, PPAR-alpha agonists such as clofibrate and gemfibrozil, PPAR-gamma agonists such as thiazolidinediones (e.g. rosiglitazone and pioglitazone, alpha-glucosidase inhibitors such as acarbose (which inhibit starch digestion), and prandial insulin releasers such as repaglinide. The amounts of complementary agents combined with compounds of the invention in single formulations are in accord with the doses used in standard clinical practice. Established safe and effective dose ranges for certain representative compounds are set forth above.

The invention will be better understood by reference to the following examples which illustrate but do not limit the invention described herein.

EXAMPLES

Example 1

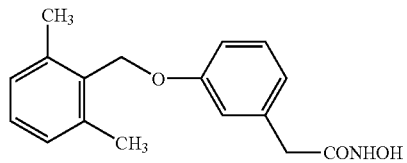

N-Hydroxy-2-[3-(2,6-dimethylbenzyloxy)phenyl]acetamide

Step A: Preparation of Ethyl 3-hydroxyphenylacetate

A solution of 3-Hydroxyphenylacetic acid (25 g, 164.31 mmol) and p-Toluenesulfonic acid monohydrate (3.49 g, 18.3 mmol) in abs ethanol (250 ml) was refluxed for 4 hours or until all the starting material is consumed. The reaction mixture was concentrated, diluted with ethyl acetate and washed with water. The organic layer was dried over $Na_2SO_4$, filtered, concentrated, and purified by flash chromatography on a silica gel column (hex:ethyl acetate 2:1) to give the title compound.

$^1$H NMR (270 MHz, $CDCl_3$): 1.2 (t, 3H); 3.5 (s, 2H); 4.1 (q, 2H); 6.6-7.2 (m, 4H).

Step B: Preparation of Ethyl 3-(2,6-dimethylbenzyloxy)phenylacetate

A solution of 2,6-Dimethylbenzyl alcohol (5.25 g, 38.6 mmol) and diisopropyl azodicarboxylate (DIAD, 8.49 g, 42 mmol) in THF (30 ml) and DMF (13 ml) was added drop wise to a solution of Ethyl 3-hydroxyphenylacetate (Step A, 6.66 g, 37 mmol) and triphenylphosphine (11 g, 42 mmol) in THF (100 ml). The reaction mixture was stirred at room temperature for 4 hours, diluted with ether and washed with water. The organic layer was dried over $Na_2SO_4$, filtered, concentrated, and purified by flash chromatography on a silica gel column (hex:ethyl acetate 1:1) to give the title compound.

$^1$H NMR (270 MHz, $CDCl_3$): 1.2 (t, 3H); 2.4 (s, 6H); 3.5 (s, 2H); 4.1 (q, 2H); 5.1 (s, 2H); 6.9 (m, 2H); 7.15-7.35 (m, 5H).

Step C: Preparation of 3-(2,6-Dimethylbenzyloxy)phenylacetic acid

To a stirred solution of Ethyl 3-(2,6-dimethylbenzyloxy) phenylacetate (Step B, 4 g, 13.6 mmol) in absolute ethanol (30 ml) was added 1N NaOH (20 ml) at room temperature. The reaction mixture was stirred for 3 hours, acidified by 1N HCl, and concentrated. The residue was taken into chloroform and washed with 0.1N HCl, dried over $Na_2SO_4$, filtered, concentrated and purified by flash chromatography on a silica gel column (hex:ethyl acetate 1:1) to give the title compound.

$^1$H NMR (270 MHz, $CDCl_3$): 2.4 (s, 6H); 3.65 (s, 2H); 5.1 (s, 2H); 6.9 (m, 2H); 7.15-7.35 (m, 5H).

Step D: Preparation of N-Hydroxy-2-[3-(2,6-dimethylbenzyloxy)phenyl]acetamide

To a stirred solution of 3-(2,6-Dimethylbenzyloxy)phenylacetic acid (Step C, 2.06 g, 7.6 mmol) in methylene chloride (20 ml) at 0° C., oxalyl chloride (1.49 g, 11.9 mmol) was added in a dropwise manner. The reaction mixture was stirred at room temperature for 2 hours. Simultaneously, in a separate flask, a mixture of hydroxylamine hydrochloride (2.98 g, 43 mmol) and triethylamine (10 ml) was stirred in THF/water (5:1, 45 ml) at 0° C. for 1-2 hours. At the end of 2 hours, the oxalyl chloride reaction mixture was concentrated and the yellow residue was dissolved in methylene chloride (10 ml). The mixture was added slowly to the hydroxylamine mixture at 0° C. The reaction mixture was stirred for 24 hours, and concentrated. The residue was taken into chloroform and washed with water, dried over $Na_2SO_4$, filtered, concentrated and purified by flash chromatography on a silica gel column (chloroform:methanol, 92.5:7.5 spiked with acetic acid) to give the title compound.

$^1$H NMR (270 MHz, $CDCl_3$): 2.4 (s, 6H); 3.5 (s, 2H); 5.1 (s, 2H); 6.85-7.0 (m, 3H); 7.15-7.35 (m, 4H).

Example 2

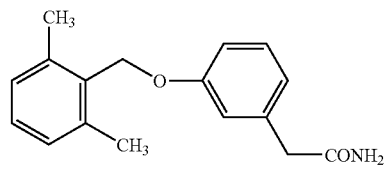

2-[3-(2,6-Dimethylbenzyloxy)phenyl]acetamide

Step A: Preparation of Ethyl 3-hydroxyphenylacetate

Using the method of Example 1, Step A, the title compound was obtained.

$^1$H NMR (270 MHz, $CDCl_3$): 1.2 (t, 3H); 3.5 (s, 2H); 4.1 (q, 2H); 6.6-7.2 (m, 4H).

Step B: Preparation of Ethyl 3-(2,6-dimethylbenzyloxy)phenylacetate

Using the method of Example 1, Step B, the title compound was obtained.
$^1$H NMR (270 MHz, CDCl$_3$): 1.2 (t, 3H); 2.4 (s, 6H); 3.5 (s, 2H); 4.1 (q, 2H); 5.1 (s, 2H); 6.9 (m, 2H); 7.15-7.35 (m, 5H).

Step C: Preparation of 3-(2,6-Dimethylbenzyloxy)phenylacetic acid:

Using the method of Example 1, Step C, the title compound was obtained.
$^1$H NMR (270 MHz, CDCl$_3$): 2.4 (s, 6H); 3.65 (s, 2H); 5.1 (s, 2H); 6.9 (m, 2H); 7.15-7.35 (m, 5H).

Step D: Preparation of 2-[3-(2,6-Dimethylbenzyloxy)phenyl]acetamide

To a stirred solution of 3-(2,6-Dimethylbenzyloxy)phenylacetic acid (3.08 g, 11.4 mmol) and Benzotriazol-1-yloxy-tris(dimethylamino)-phosphonium hexafluorophosphate (5.05 g, 11.4 mmol) in DMF (75 ml) was added triethylamine (2.30 g, 22.8 mmol), and the reaction mixture was stirred for 1 h at room temperature. To this reaction mixture was added liquid ammonia (100 ml) at −40 0° C., the resulting mixture was allowed to warm to ambient temperature over 10-12 hours and concentrated. The residue was taken into ethyl acetate and washed with water (2×), dried over Na$_2$SO$_4$, filtered, concentrated and purified by flash chromatography on a silica gel column (ethyl acetate:hexane, 2.5:1 spiked with acetic acid) to give the title compound.
$^1$H NMR (270 MHz, CDCl$_3$): 2.4 (s, 6H); 3.6 (s, 2H); 5 (s, 2H); 5.55 (br, 1H); 6.9 (m, 3H); 7.1-7.2 (m, 3H); 7.3 (t, 1H).

Example 3

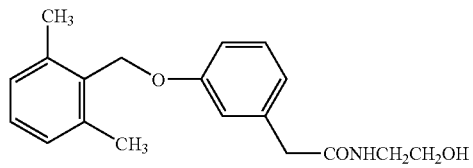

N-(2-Hydroxyethyl)-2-[3-(2,6-dimethylbenzyloxy)phenyl]acetamide

Step A: Preparation of Ethyl 3-hydroxyphenylacetate

Using the method of Example 1, Step A, the title compound was obtained.
$^1$H NMR (270 MHz, CDCl$_3$): 1.2 (t, 3H); 3.5 (s, 2H); 4.1 (q, 2H); 6.6-7.2 (m, 4H).

Step B: Preparation of Ethyl 3-(2,6-dimethylbenzyloxy)phenylacetate

Using the method of Example 1, Step B, the title compound was obtained.
$^1$H NMR (270 MHz, CDCl$_3$): 1.2 (t, 3H); 2.4 (s, 6H); 3.5 (s, 2H); 4.1 (q, 2H); 5.1 (s, 2H); 6.9 (m, 2H); 7.15-7.35 (m, 5H).

Step C: Preparation of 3-(2,6-Dimethylbenzyloxy)phenylacetic acid

Using the method of Example 1, Step C, the title compound was obtained.
$^1$H NMR (270 MHz, CDCl$_3$): 2.4 (s, 6H); 3.65 (s, 2H); 5.1 (s, 2H); 6.9 (m, 2H); 7.15-7.35 (m, 5H).

Step D: Preparation of N-(2-Hydroxyethyl)-2-[3-(2,6dimethylbenzyloxy)phenyl]acetamide To a stirred solution of 3-(2,6-Dimethylbenzyloxy)phenylacetic acid (Step C, 6.0 g, 22.2 mmol), 1-Hydroxybenzotriazole (7.19 g, 53.2 mmol), and Ethanolamine (2.70 g, 44.2 mmol) in methylene chloride (30 ml) and DMF (5 ml) was added EDCI (7.66 g, 40 mmol) at 0° C., the resulting reaction mixture was stirred at room temperature for 24 hours and concentrated under reduced pressure. The residue was dissolved in methylene chloride (10 ml) and washed with NaHCO$_3$, 0.1M HCl, brine, dried over Na$_2$SO$_4$, filtered, concentrated and purified by flash chromatography on a silica gel column (chloroform:methanol, 9:1) to provide the title compound.
$^1$H NMR (270 MHz, CDCl$_3$): 2.4 (s, 6H); 3.4 (q, 2H); 3.65 (s, 2H); 3.7 (t, 2H); 5.05 (s, 2H); 6.0 (b, 1H); 6.9-7.0 (m, 3H); 7.05-7.2 (m, 3H); 7.3 (t, 1H).

Example 4

Compound CT and Compound CV Reduced Hyperglycemia and Hyperlipidemia and Hepatic Transaminases in Serum from Ob/Ob Mice Ob/ob mice have a defect in the gene for leptin, a protein involved in appetite regulation and energy metabolism, and are hyperphagic, obese, and insulin resistant. They develop hyperglycemia and fatty liver.

Male ob/ob mice were divided into four treatment groups comprising six mice each, and given daily oral doses of Vehicle (1% hydroxypropylmethylcellulose) or 100 mg/kg Compound CT, Compound CV, or Compound BI (a positive control) for two weeks. Blood samples were collected form the retro-orbital sinus and processed for serum chemistry measurements.

As shown in Table 1, Compound CT, Compound CV, and Compound BI blood glucose, triglycerides, and free fatty acids in serum, versus vehicle-treated mice. As shown in Table 2, serum insulin was also reduced relative to vehicle by these three compounds, consistent with reversal of insulin resistance (and consequent compensatory insulin hypersecretion).

TABLE 1

Effect of Compound CT, Compound CV, and Compound BI on serum glucose, triglycerides, and free fatty acids in ob/ob mice

| Group | Glucose ± SD (mg/dL) | Triglycerides ± SD (mg/dL) | Free Fatty Acids ± SD (μM) |
|---|---|---|---|
| Vehicle | 191 ± 26 | 84 ± 2 | 1392 ± 78 |
| CT | 131 ± 21 | 68 ± 6 | 894 ± 55 |
| CV | 164 ± 10 | 73 ± 5 | 1070 ± 60 |
| BI | 180 ± 19 | 58 ± 2 | 874 ± 74 |

TABLE 2

Effect of Compound CT, Compound CV, and Compound BI on serum insulin in ob/ob mice

| Group | Insulin ± SD (ng/ml) |
|---|---|
| Vehicle | 13.9 ± 2.4 |
| CT | 3.1 ± 0.9 |
| CV | 5.0 ± 0.7 |
| BI | 1.1 ± 0.2 |

Example 5

Treatment with Compound CT, Compound CV, and Compound BI Reduced Serum Alt and Ast Versus Vehicle-Treated Ob/Ob Mice Obese ob/ob mice develop chronic inflammatory fatty liver disease and are considered to be an animal model for nonalcoholic steatohepatitis (NASH), a condition which can lead toward progressive cirrhosis and liver dysfunction. In NASH, fat accumulation increases the susceptibility of the liver to inflammatory injury. One characteristic sign of NASH in patients is, in the absence of viral infection or alcoholism, elevated levels in serum of enzymes that are released from damaged hepatocytes, e.g. alanine aminotransferase (ALT) and Aspartate-aminotransferase (AST). These enzymes are elevated in ob/ob mice as a consequence of fatty liver and secondary inflammation. In Table 3, ALT and AST in serum samples from mice treated with Compound CT, Compound CV, and Compound BI are shown, as are enzyme levels in serum from control ob/ob mice treated only with vehicle. Treatment with Compound CT, Compound CV, and Compound BI reduced serum ALT and AST versus vehicle-treated ob/ob mice.

TABLE 3

Effect of Compound CT, Compound CV, and Compound BI on serum ALT and AST

| Group | ALT (U/L) ± SD | ST (U/L) ± SD |
|---|---|---|
| Vehicle | 501 ± 93 | 472 ± 83 |
| CT | 230 ± 59 | 170 ± 23 |
| CV | 484 ± 65 | 318 ± 48 |
| BI | 330 ± 40 | 217 ± 24 |

What is claimed is:

1. A compound of the formula:

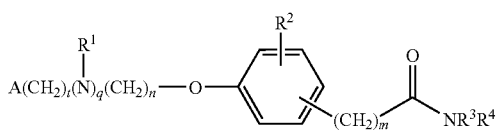

wherein
n is 1 or 2;
m is 1, 2, 3, 4 or 5;
q is 0 or 1;
t is 0 or 1;
$R^1$ is alkyl having from 1 to 3 carbon atoms;
$R^2$ is hydrogen, halo, or alkyl having from 1 to 3 carbon atoms;
$R^3$ is hydrogen or —$(CH_2)_g$OH wherein g is 0, 1 or 2;
$R^4$ is hydrogen, methyl or ethyl;
A is 2,6-dimethylphenyl;
or a pharmaceutically acceptable salt of the compound.

2. The compound or salt of claim 1, wherein the compound is represented by the formula

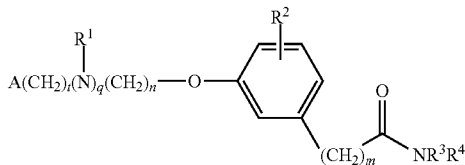

wherein A, $R^1$, $R^2$, $R^3$, $R^4$, t, q, n, and m have the values set forth in claim 1.

3. The compound or salt of claim 2, wherein m is 1; n is 1; q is 0; t is 0; $R^2$ is hydrogen; and $R^4$ is hydrogen.

4. The compound or salt of claim 3, wherein the compound is N-Hydroxy-2-[3-(2,6-dimethylbenzyloxy)phenyl]acetamide.

5. The compound or salt of claim 3, wherein the compound is 2-[3-(2,6-Dimethylbenzyloxy)phenyl]acetamide.

6. The compound or salt of claim 3, wherein the compound is N-(2-Hydroxyethyl)-2-[3-(2,6-dimethylbenzyloxy)phenyl]acetamide.

7. A method for treating a mammalian subject with a condition selected from the group consisting of insulin resistance syndrome and diabetes, comprising administering to the subject an amount of a compound of the formula:

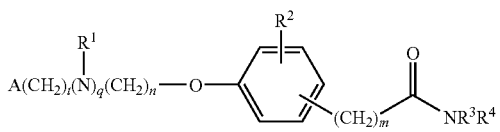

wherein
n is 1 or 2;
m is 0, 1, 2, 3, 4 or 5;
q is 0 or 1;
t is 0 or 1;
$R^1$ is alkyl having from 1 to 3 carbon atoms;
$R^2$ is hydrogen, halo, alkyl having from 1 to 3 carbon atoms, or alkoxy having from 1 to 3 carbon atoms;
$R^3$ is hydrogen or —$(CH_2)_g$OH wherein g is 0, 1 or 2;
$R^4$ is hydrogen, methyl or ethyl;
A is phenyl, substituted by 1 or 2 groups selected from: halo, alkyl having 1 or 2 carbon atoms, perfluoromethyl, alkoxy having 1 or 2 carbon atoms, and perfluoromethoxy; or
cycloalkyl having from 3 to 6 ring carbon atoms wherein the cycloalkyl is unsubstituted or one or two ring carbons are independently mono-substituted by methyl or ethyl;
or a pharmaceutically acceptable salt of the compound.

8. The method of claim 7, wherein the compound is represented by the formula

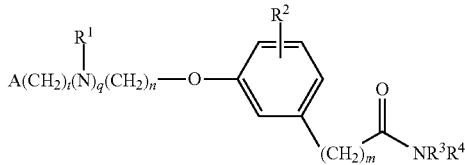

wherein A, $R^1$, $R^2$, $R^3$, $R^4$, t, q, n, and m have the values set forth in claim 7.

9. The method of claim 8, wherein m is 1; n is 1; q is 0; t is 0; $R^2$ is hydrogen; $R^4$ is hydrogen; and
A is phenyl, substituted by 1 or 2 groups selected from: halo, alkyl having 1 or 2 carbon atoms, perfluoromethyl, alkoxy having 1 or 2 carbon atoms, and perfluoromethoxy.

10. The method of claim 9, wherein A is 2,6-dimethylphenyl.

11. The method of claim 10, wherein the compound is N-Hydroxy-2-[3-(2,6-dimethylbenzyloxy)phenyl]acetamide.

12. The method of claim 10, wherein the compound is 2-[3-(2,6-Dimethylbenzyloxy)phenyl]acetamide.

13. The method of claim 10, wherein the compound is N-(2-Hydroxyethyl)-2-[3-(2,6-dimethylbenzyloxy)phenyl]acetamide.

14. The method of claim 7, wherein the subject is a human.

15. The method of claim 14, wherein the compound or salt is administered orally in an amount from one milligram to four hundred milligrams per day.

16. The method of claim 7, wherein the condition is insulin resistance syndrome or Type II Diabetes.

17. A pharmaceutical composition adapted for oral administration, comprising a pharmaceutically acceptable carrier and from one milligram to four hundred milligrams of a compound of the formula:

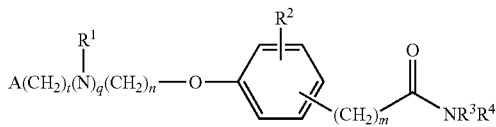

I wherein
n is 1 or 2;
m is 1, 2, 3, 4 or 5;
q is 0 or 1;
t is 0 or 1;
$R^1$ is alkyl having from 1 to 3 carbon atoms;
$R^2$ is hydrogen, halo, alkyl having from 1 to 3 carbon atoms, or alkoxy having from 1 to 3 carbon atoms;
$R^3$ is hydrogen or —$(CH_2)_g$OH wherein g is 0, 1 or 2;
$R^4$ is hydrogen, methyl or ethyl;
A is 2,6-dimethylphenyl;
or a pharmaceutically acceptable salt of the compound.

18. The pharmaceutical composition of claim 17, wherein the compound is represented by the formula

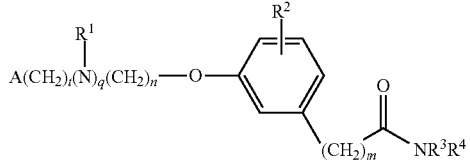

wherein A, $R^1$, $R^2$, $R^3$, $R^4$, t, q, n, and m have the values set forth in claim 17.

19. The pharmaceutical composition of claim 18, wherein m is 1; n is 1; q is 0; t is 0; $R^2$ is hydrogen; and $R^4$ is hydrogen.

20. The pharmaceutical composition of claim 19, wherein the compound is N-Hydroxy-2-[3-(2,6-dimethylbenzyloxy)phenyl]acetamide.

21. The pharmaceutical composition of claim 19, wherein the compound is 2-[3-(2,6-Dimethylbenzyloxy)phenyl]acetamide.

22. The pharmaceutical composition of claim 19, wherein the compound is N-(2-Hydroxyethyl)-2-[3-(2,6-dimethylbenzyloxy)phenyl]acetamide.

23. The pharmaceutical composition of claim 17 in oral dosage form.

* * * * *